(12) United States Patent
Cho et al.

(10) Patent No.: US 9,581,498 B2
(45) Date of Patent: Feb. 28, 2017

(54) ROTATING-ELEMENT SPECTROSCOPIC ELLIPSOMETER AND METHOD FOR MEASUREMENT PRECISION PREDICTION OF ROTATING-ELEMENT SPECTROSCOPIC ELLIPSOMETER, RECORDING MEDIUM STORING PROGRAM FOR EXECUTING THE SAME, AND COMPUTER PROGRAM STORED IN MEDIUM FOR EXECUTING THE SAME

(71) Applicant: Korea Research Institute of Standards and Science, Daejeon (KR)

(72) Inventors: Yong Jai Cho, Daejeon (KR); Won Chegal, Daejeon (KR); Hyun Mo Cho, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 14/969,096

(22) Filed: Dec. 15, 2015

(65) Prior Publication Data

US 2016/0169742 A1  Jun. 16, 2016

(30) Foreign Application Priority Data

Dec. 16, 2014  (KR) .................. 10-2014-0180875

(51) Int. Cl.
*G01J 4/00* (2006.01)
*G01J 3/447* (2006.01)
(Continued)

(52) U.S. Cl.
CPC .............. *G01J 3/447* (2013.01); *G01J 4/04* (2013.01); *G01N 21/211* (2013.01); *G01N 2021/213* (2013.01)

(58) Field of Classification Search
CPC ..... G01J 3/447; G01J 3/04; G01J 4/00; B05D 3/06; G01B 11/00; G01N 21/21
See application file for complete search history.

(56) References Cited

U.S. PATENT DOCUMENTS

| 5,354,575 A | * | 10/1994 | Dagenais | ............ C23C 14/547 204/192.13 |
| 8,830,463 B2 | | 9/2014 | Cho et al. | |
| 2013/0044318 A1 | * | 2/2013 | Cho | ..................... G01N 21/211 356/369 |

FOREIGN PATENT DOCUMENTS

KR    1020130019495 A    2/2013

OTHER PUBLICATIONS

Cho et al., "Quantifying Ellipsometric Data Uncertainties for Multichannel Rotating-Element Ellipsometers," Hosted by 2014 SPIE Optics + Phonotics, Aug. 20, 2014.

* cited by examiner

*Primary Examiner* — Tarifur Chowdhury
*Assistant Examiner* — Jamil Ahmed
(74) *Attorney, Agent, or Firm* — The Webb Law Firm

(57) ABSTRACT

Provided are a rotating-element spectroscopic ellipsometer and a method for measurement precision prediction of a rotating-element spectroscopic ellipsometer, a recording medium storing program for executing the same, and a computer program stored in a medium for executing the same, and more particularly, a rotating-element spectroscopic ellipsometer and a method for measurement precision prediction of a rotating-element spectroscopic ellipsometer capable of calculating the measurement precision of the rotating-element spectroscopic ellipsometer based on a theoretical equation on standard deviations of ellipsometric parameters for a sample, a recording medium storing pro- (Continued)

gram for executing the same, and a computer program stored in a medium for executing the same.

9 Claims, 4 Drawing Sheets

(51) Int. Cl.
*G01J 4/04* (2006.01)
*G01N 21/21* (2006.01)

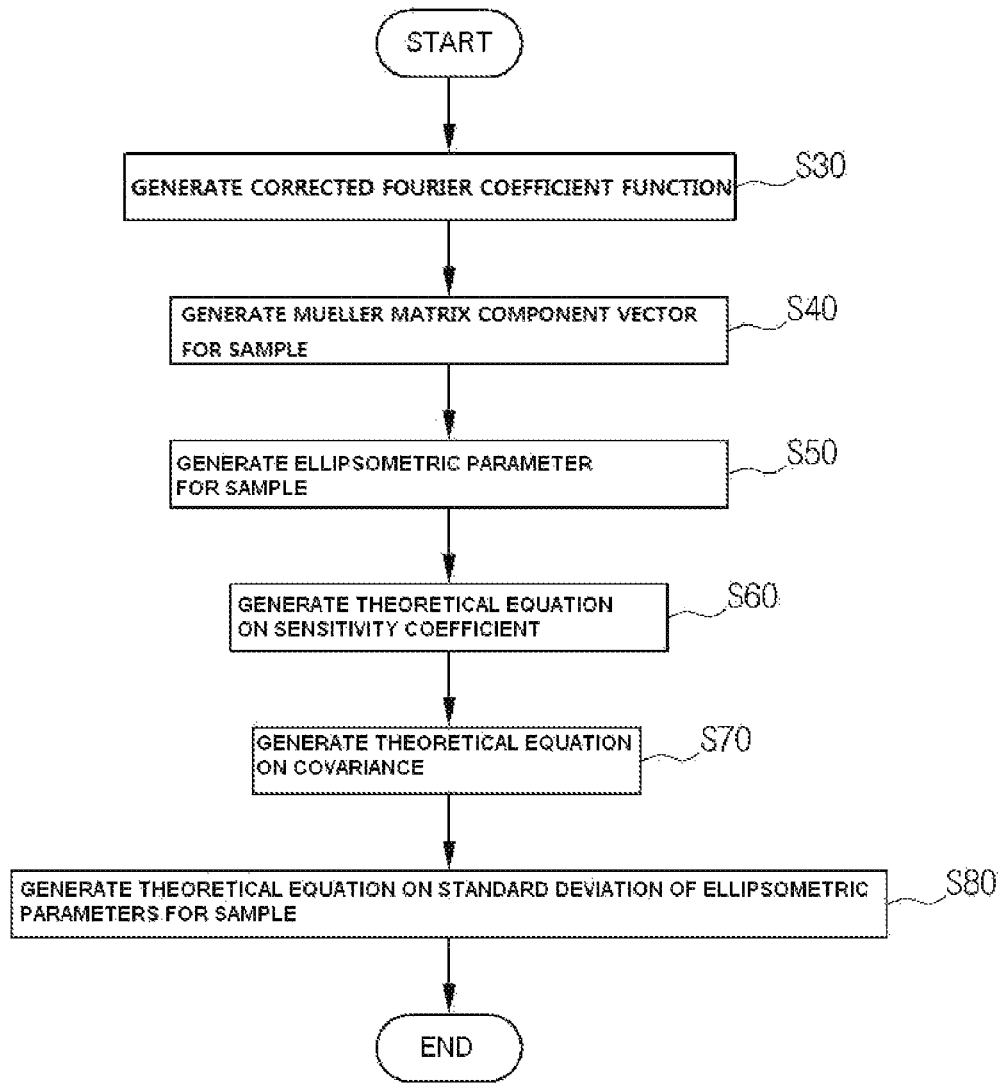

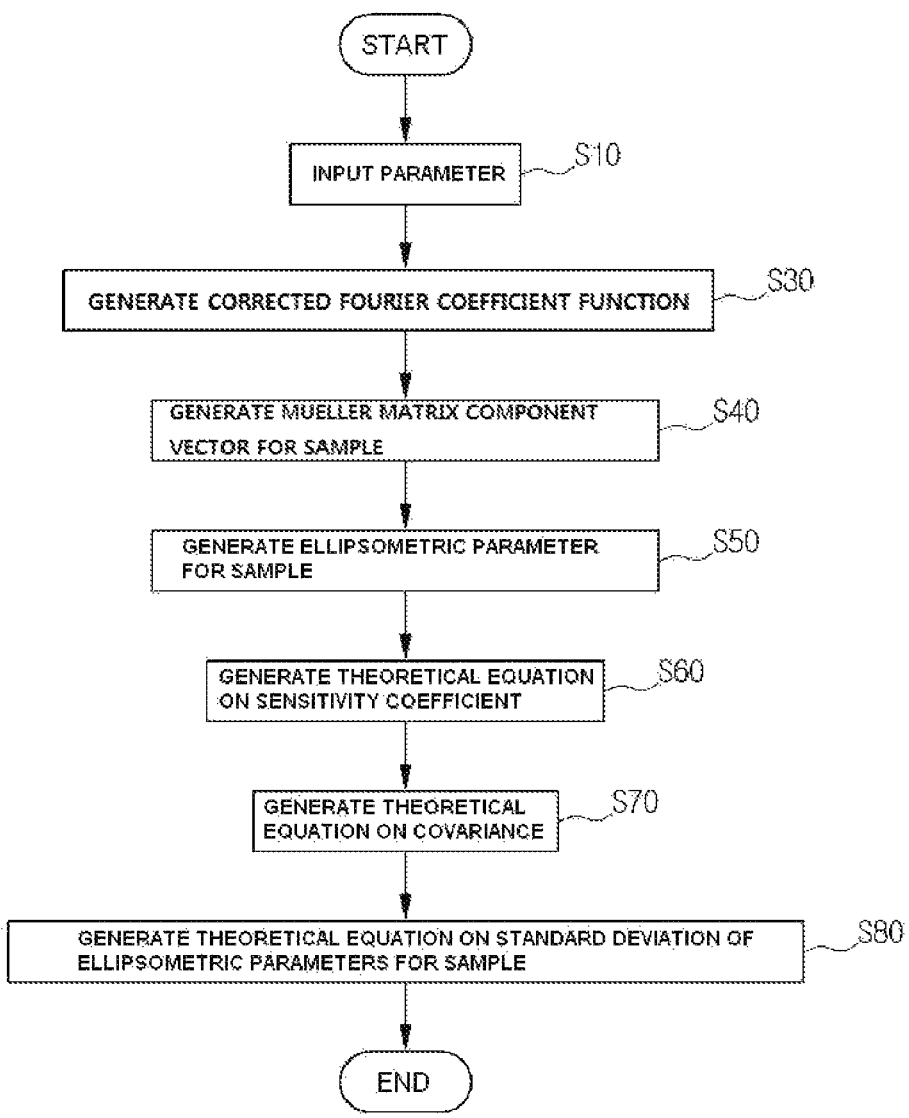

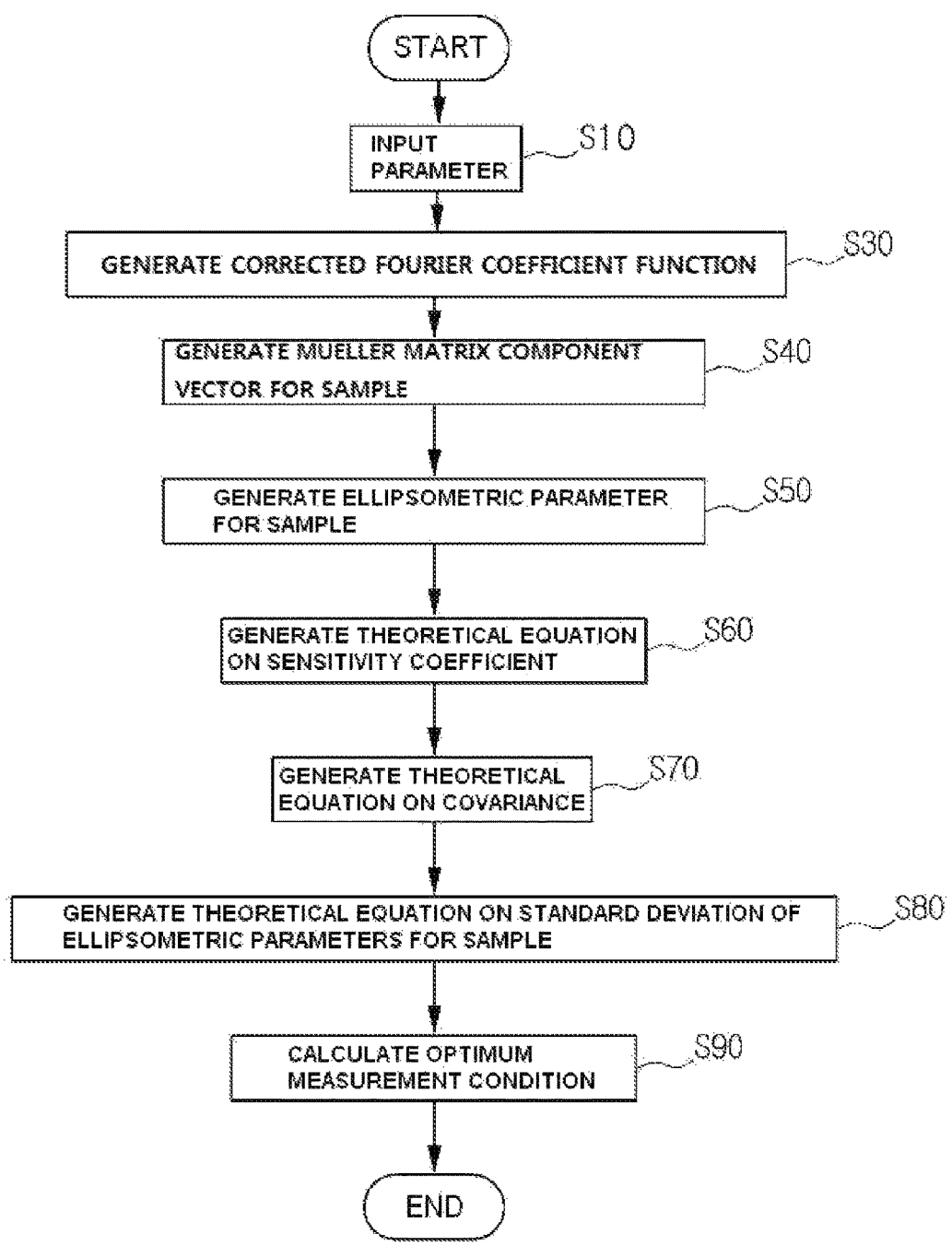

_____

ROTATING-ELEMENT SPECTROSCOPIC ELLIPSOMETER AND METHOD FOR MEASUREMENT PRECISION PREDICTION OF ROTATING-ELEMENT SPECTROSCOPIC ELLIPSOMETER, RECORDING MEDIUM STORING PROGRAM FOR EXECUTING THE SAME, AND COMPUTER PROGRAM STORED IN MEDIUM FOR EXECUTING THE SAME

CROSS-REFERENCE TO RELATED APPLICATION

This application claims priority to Korean Patent Application No. 10-2014-0180875 filed Dec. 16, 2014, the disclosure of which is hereby incorporated in its entirety by reference.

TECHNICAL FIELD

The following disclosure relates to a rotating-element spectroscopic ellipsometer and a method for measurement precision prediction of a rotating-element spectroscopic ellipsometer, a recording medium storing a program for executing the same, and a computer program stored in a medium for executing the same, and more particularly, to a rotating-element spectroscopic ellipsometer and a method for measurement precision prediction of a rotating-element spectroscopic ellipsometer capable of calculating the measurement precision of the rotating-element spectroscopic ellipsometer based on a theoretical equation on standard deviations of ellipsometric parameters for a sample, a recording medium storing program for executing the same, and a computer program stored in a medium for executing the same.

BACKGROUND

In industrial fields associated with a semiconductor device, a flat panel display, a nano-bio, a nano-imprint, thin film optics, and the like, that have been rapidly developed, importance of a technology capable of non-destructively and contactlessly measuring and evaluating physical properties such as a thicknesses of a thin film of nano samples, a shape of a nano pattern, and the like, in a manufacturing process step has gradually increased.

Various multi-channel rotating-element spectroscopic ellipsometers (RE-SEs) have excellent measurement abilities like high-precision, real-time, non-destructive, and contactless schemes, and as a result have been widely used in a semiconductor manufacturing process. With the development of semiconductor device process technologies, the thickness of the thin film used for these technologies is getting smaller and smaller and thus reaches a level of atomic layer and the shape of the nano pattern is changed from a two-dimensional structure into a three-dimensional structure and thus is becoming increasingly complicated. Therefore, for the rotating-element spectroscopic ellipsometer to be continuously used as a measurement tool for next-generation semiconductor industries, it is important to continuously enhance measurement uncertainty.

There are currently no methods generally accepted to assess measurement uncertainty for an RE-SE. In 2004, Aspnes derives a theoretical equation on assessing the measurement uncertainty for the RE-SEs using a non-integral photodetector. However, the derived theoretical equation may not be applied for assessing uncertainty for state-of-the-art multi-channel RE-SEs which have been widely used in the semiconductor industries. The reason is that the state-of-the-art multi-channel RE-SEs use an integral photodetector like a CCD array for real-time measurement. Recently, the research paper published by Johs and Herzinger proves that it is practically impossible to produce a standard sample having micro defects which may not be analyzed even with the measurement precision of the state-of-the-art multi-channel RE-SEs. Therefore, a new method for quantifying measurement uncertainty which does not depend on a measurement sample has been proposed. However, the method for quantifying measurement uncertainty essentially requires measurement values of several incident angles. However, the RE-SEs used in the semiconductor industries use the fixed incident angle and therefore the method for assessing measurement uncertainty thereof has not widely been used. For another reason, a silicon wafer, a gold substrate, and a fused silica substrate which are used to assess the measurement uncertainty always have non-ideal physical properties such as surface roughness and interface layer basically.

Therefore, there is a need to develop a rotating-element spectroscopic ellipsometer capable of solving the above-mentioned problems.

Korean Patent Laid-Open Publication No. 10-2013-0019495 discloses a rotating-element spectroscopic ellipsometer and a method for measuring physical properties of a sample using the same.

RELATED ART DOCUMENT

Patent Document

Korean Patent Laid-Open Publication No. 10-2013-0019495 (Published Date: Feb. 27, 2013)

SUMMARY

An embodiment of the present invention is directed to providing a method for calculating a theoretical model equation which may be applied to various kinds of multi-channel RE-SEs and may determine a measurement limitation thereof, that is, a theoretical equation on standard deviations of ellipsometric parameters for a sample and a rotating-element spectroscopic ellipsometer for applying a theoretical equation on standard deviations of ellipsometric parameters for a sample.

In one general aspect, a rotating-element spectroscopic ellipsometer (RE-SE) includes: a light source 100 radiating an incident light 110 toward a sample 10; a polarization state generator 200 disposed between the light source 100 on a traveling path of the incident light 110 and the sample 10 and controlling a polarized state of the incident light 110 radiated from the light source 100; a polarization state analyzer 300 receiving reflected light (or transmitted light) 120 having a changed polarization state while the incident light 100 is polarized by passing through the polarization state generator 200 and then reflected (or transmitted) by the sample 10 and analyzing a change in the polarization state of the reflected light (or transmitted light) 120; a photodetector element 400 receiving the reflected light (or the transmitted light) 120 passing through the polarization state analyzer 300 and measuring irradiance of the incident light with an electrical signal of a voltage or a current; and an arithmetic unit 500 calculating measurement precision of the rotating-element spectroscopic ellipsometer (RE-SE) based on a theoretical equation on standard deviations of ellipsometric parameters for the sample, wherein a plurality of rotatable elements configured of a linear polarizer and a compensator are disposed in the polarization state generator 200 or the polarization state analyzer 300 and at least one of the rotatable elements includes a constantly rotating element rotating at a uniform velocity and the rest rotatable elements other than the constantly rotating element are a scanning element and move to a predefined azimuth to stop upon the measurement.

When the rotatable elements all consist of linear polarizers the ellipsometric parameters for the isotropic sample may be selected as $[N_{SP}=-(m_{12}+m_{21})/2, C_{SP}=(m_{33}+m_{44})/2]$ where $M_{jk}$ is Mueller matrix components and $m_{jk}=M_{jk}/M_{11}$ normalized Mueller matrix components. When at least one of the rotatable elements is configured of compensators the ellipsometric parameters for the isotropic sample may be selected as $[N_{SP}=(m_{12}+m_{21})/2, C_{SP}=(m_{33}+m_{44})/2, S_{SP}=(m_{34}-m_{43})/2]$.

The arithmetic unit 500 may define Fourier coefficients of an irradiance waveform depending on the change in azimuth of the constantly rotating element as a function of constant values $\kappa$, $d_{12}$, $d_{13}$, $l_1$, and $l_2$ of common factors, optical properties (a refractive index, the thickness of the thin film, the shape and dimension of the nano pattern) of the sample, azimuths $\theta$ of the scanning elements, phase differences $\delta$ of the compensators, an incident angle $\phi$, and a measurement wavelength $\lambda$, derive a theoretical equation on Mueller matrix components of the sample from theoretical equations on the Fourier coefficients, define a theoretical equation on the ellipsometric parameters for the sample from the theoretical equation on the Mueller matrix components of the sample, define theoretical equations on sensitivity coefficients from the theoretical equation on the ellipsometric parameters for the sample, define a theoretical equation on the covariance for the Fourier coefficients as a function of a measurement frequency N required for computation of the Fourier coefficient, a measurement frequency J of exposure per one rotating period, a mechanical rotating period T of the constantly rotating element, a delay time $T_d$, an integration time $T_i$, a scaling coefficient $\eta$, and the theoretical equations on the Fourier coefficients, and calculate the theoretical equation on the standard deviations of the ellipsometric parameters for the sample from the theoretical equations on the covariance for the Fourier coefficients and the theoretical equations on the sensitivity coefficients.

The theoretical equation on the standard deviations of the ellipsometric parameters for the sample may depend on the following Equation.

$$\sigma(\langle Q \rangle) = \left[ \sum_{j=1}^{2N_{ho}+1} c_{Q,X_j}^2 \mathrm{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \mathrm{cov}(\langle X_j \rangle, \langle X_k \rangle) \right]^{1/2}$$

When the rotatable elements all may be configured of the linear polarizer one may calculate the ellipsometric parameters for the isotropic sample defined like $N_{SP}=(m_{12}+m_{21})/2$, $C_{SP}=(m_{33}+M_{44})/2$ from the plurality of Fourier coefficients and analyze physical properties for the sample of at least any one of interface characteristics, the thickness of the thin film, a complex refractive index, a nano shape, anisotropy characteristics, surface roughness, a composition ratio, and crystallinity based on the calculated ellipsometric parameters. When at least one of the rotatable elements may be configured of the compensators one may calculate the ellipsometric parameters for the isotropic sample defined like $N_{SP}=(m_{12}+m_{21})/2$, $C_{SP}=(m_{33}+m_{44})/2$, $S_{SP}=(m_{34}-m_{43})/2$ from the plurality of Fourier coefficients and analyze physical properties for the sample of at least any one of interface characteristics, the thickness of the thin film, a complex refractive index, a nano shape, anisotropy characteristics, surface roughness, a composition ratio, and crystallinity based on the calculated ellipsometric parameters.

In another general aspect, a method for measurement precision prediction of a rotating-element spectroscopic ellipsometer for calculating the measurement precision of the rotating-element spectroscopic ellipsometer including a light source 100, a polarization state generator 200, a polarization state analyzer 300, a photodetector element 400, and an arithmetic unit 500, in which the polarization state generator 200 or the polarization state analyzer 300 includes a plurality of rotatable elements and the rotatable elements include constantly rotating elements rotating at a uniform velocity and scanning elements, the method includes: generating a function of corrected Fourier coefficients X consisting of constant values $\kappa$, $d_{12}$, $d_{13}$, $l_1$ and $l_2$ of common factors, optical properties (a refractive index, a thickness of a thin film, a shape and a dimension of a nano pattern) of a sample, azimuths $\theta$ of the scanning elements, phase differences $\delta$ of compensators, an incident angle $\phi$, and a measurement wavelength $\lambda$ (S30); generating a Mueller matrix component vector $V^{(SP)}(X)$ of the sample consisting of the function of the corrected Fourier coefficients X (S40); generating an ellipsometric parameter Q(X) of the sample consisting of the function of the corrected Fourier coefficients X from Mueller matrix vector components obtained in the generating of the Mueller matrix component vector (S40) (S50); generating a theoretical equation on a sensitivity coefficient using the function of the corrected Fourier coefficients X using a differential of $c_{Q,X_j} = \partial Q/\partial X_j$ from the ellipsometric parameter Q(X) of the sample generated in the generating of the ellipsometric parameter (S50) (S60); generating a theoretical equation on a covariance of the corrected Fourier coefficients X (S70); and generating a theoretical equation $\sigma(\langle Q \rangle)$ on standard deviations of ellipsometric parameters Q(X) consisting of a function of a measurement frequency N required for computation of the Fourier coefficient, a measurement frequency J of exposure per one rotating period, a mechanical rotating period T of the constantly rotating element, an integration time $T_i$, a scaling coefficient $\eta$, and the corrected Fourier coefficients X by substituting results of the generating of the theoretical equation on the sensitivity coefficient (S60) and the generating of the theoretical equation on the covariance (S70) into the following Equation (S80).

$$\sigma(\langle Q \rangle) = \left[ \sum_{j=1}^{2N_{ho}+1} c_{Q,X_j}^2 \mathrm{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \mathrm{cov}(\langle X_j \rangle, \langle X_k \rangle) \right]^{1/2}$$

(In the above Equation, the theoretical equation on the corrected Fourier coefficients X is obtained from the generating of the function of the corrected Fourier coefficient (S30)).

The function of the corrected Fourier coefficients X in the generating of the function of the corrected Fourier coefficient (S30) may depend on the following Equation.

$$I_0 = \gamma \sum_{j=1}^{u} \sum_{k=1}^{v} i_{0,jk} M_{jk} = \gamma i_0 \cdot V^{(SP)}$$

$$A_n = \gamma \sum_{j=1}^{u} \sum_{k=1}^{v} a_{n,jk} M_{jk} = \gamma a_n \cdot V^{(SP)}$$

$$B_n = \gamma \sum_{j=1}^{u} \sum_{k=1}^{v} b_{n,jk} M_{jk} = \gamma b_n \cdot V^{(SP)}$$

In the above Equations, $\gamma = \kappa(1 + d_{12} \cos 2A + d_{13} \sin 2A)(1 + l_1 \cos 2P + l_2 \sin 2P)$, $\kappa = c\epsilon_0 \eta_{QE} A_{PDE} T_{PSA} T_{PSG} D_{11} L_0 / 2$, $d_{12(13)} = D_{12(13)}/D_{11}$, $l_{1(2)} = L_{1(2)}/L_0$.

The Mueller matrix component vector $V^{(SP)}(X)$ of the sample in the generating of the Mueller matrix component vector (S40) may depend on the following Equation.

$V^{(SP)} = (\Omega^T \Omega)^{-1} \Omega^T X$, (Here, $\Omega = \gamma(i_0, a_1, a_2, b_2, \ldots, a_{N_{ho}}, b_{N_{ho}})^T$, $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$, $b_n = (\partial B_n/\partial M_{11}, \ldots, \partial B_n/\partial M_{1v}, \ldots, \partial B_n/\partial M_{u1}, \ldots, \partial B_n/\partial M_{uv})/\gamma$), The relational equation on the covariance between the corrected Fourier coefficients X and the uncorrected Fourier coefficients X' in the generating of the theoretical equation on the covariance (S70) may be obtained depending on $\text{cov}(\langle X_j \rangle, \langle X_k \rangle) \equiv \text{cov}(\langle X_j' \rangle, \langle X_k' \rangle)$, and the theoretical equation on the covariance for the uncorrected Fourier coefficients X' depends on the following Equation.

$$\text{cov}(\langle I_0' \rangle, \langle I_0' \rangle) = \sigma^2(\langle I_0' \rangle) = \frac{\eta}{NJT_i} \langle I_0' \rangle,$$

$$\text{cov}(\langle A_n' \rangle, \langle A_n' \rangle) = \sigma^2(\langle A_n' \rangle) = \frac{2\eta \xi_n^2}{NJT_i \sin^2 \xi_n}\left(\langle I_0' \rangle + \frac{\sin \xi_{2n}}{2\xi_{2n}} \langle A_{2n}' \rangle\right),$$

$$\text{cov}(\langle B_n' \rangle, \langle B_n' \rangle) = \sigma^2(\langle B_n' \rangle) = \frac{2\eta \xi_n^2}{NJT_i \sin^2 \xi_n}\left(\langle I_0' \rangle - \frac{\sin^2 \xi_{2n}}{2\xi_{2n}} \langle A_{2n}' \rangle\right),$$

$$\text{cov}(\langle I_0' \rangle, \langle A_n' \rangle) = \frac{\eta}{NJT_i} \langle A_n' \rangle,$$

$$\text{cov}(\langle I_0' \rangle, \langle B_n' \rangle) = \frac{\eta}{NJT_i} \langle B_n' \rangle,$$

$$\text{cov}(\langle A_n' \rangle, \langle A_m' \rangle) = \frac{\eta m \xi_n}{NJT_i \sin \xi_n \sin \xi_m}\left(\frac{\sin \xi_{n+m}}{n+m} \langle A_{n+m}' \rangle + \frac{\sin \xi_{n-m}}{n-m} \langle A_{n-m}' \rangle\right),$$

$(n \neq m)$, $$\text{cov}(\langle B_n' \rangle, \langle B_m' \rangle) = \frac{\eta m \xi_n}{NJT_i \sin \xi_n \sin \xi_m}\left(\frac{\sin \xi_{n-m}}{n-m} \langle A_{n-m}' \rangle - \frac{\sin \xi_{n+m}}{n+m} \langle A_{n+m}' \rangle\right),$$

$(n \neq m)$, $$\text{cov}(\langle A_n' \rangle, \langle B_m' \rangle) = \begin{cases} \frac{\eta \xi_n}{NJT_i \tan \xi_n} \langle B_{2n}' \rangle, & (n = m), \\ \frac{\eta m \xi_n}{NJT_i \sin \xi_n \sin \xi_m}\left(\frac{\sin \xi_{n+m}}{n+m} \langle B_{n+m}' \rangle - \frac{\sin \xi_{n-m}}{n-m} \langle B_{n-m}' \rangle\right), & (n \neq m), \end{cases}$$

$\xi_n = n\pi T_i/T$).

The method may further include: calculating an optimum measurement condition for finding out a position of the azimuth θ of the scanning elements or the incidence angle θ having a minimum value of Z in a measurement precision assessment function Z depending on the following Equation, when the number of measurement wavelengths $\lambda_j$ is $N_\lambda$ and the number of kinds of ellipsometric parameters $Q_k(\lambda_j)$ of the sample is $N_Q$ (S90).

$$Z = \sqrt{\frac{1}{N_\lambda N_Q} \sum_{j=1}^{N_\lambda} \sum_{k=1}^{N_Q} \sigma^2(\langle Q_k(\lambda_j) \rangle)}$$

Further, according to an exemplary embodiment of the present invention, a computer-readable recording medium stored with program for implementing the method for measurement precision prediction of a rotating-element spectroscopic ellipsometer may be provided.

Further, according to an exemplary embodiment of the present invention, a program stored in a computer-readable recording medium to implement the method for measurement precision prediction of a rotating-element spectroscopic ellipsometer may be provided.

BRIEF DESCRIPTION OF THE DRAWINGS

FIGS. 2 to 4 are flowcharts of a method for measurement precision prediction of a rotating-element spectroscopic ellipsometer according to an exemplary embodiment of the present invention.

DETAILED DESCRIPTION OF MAIN ELEMENTS

Figure 1:
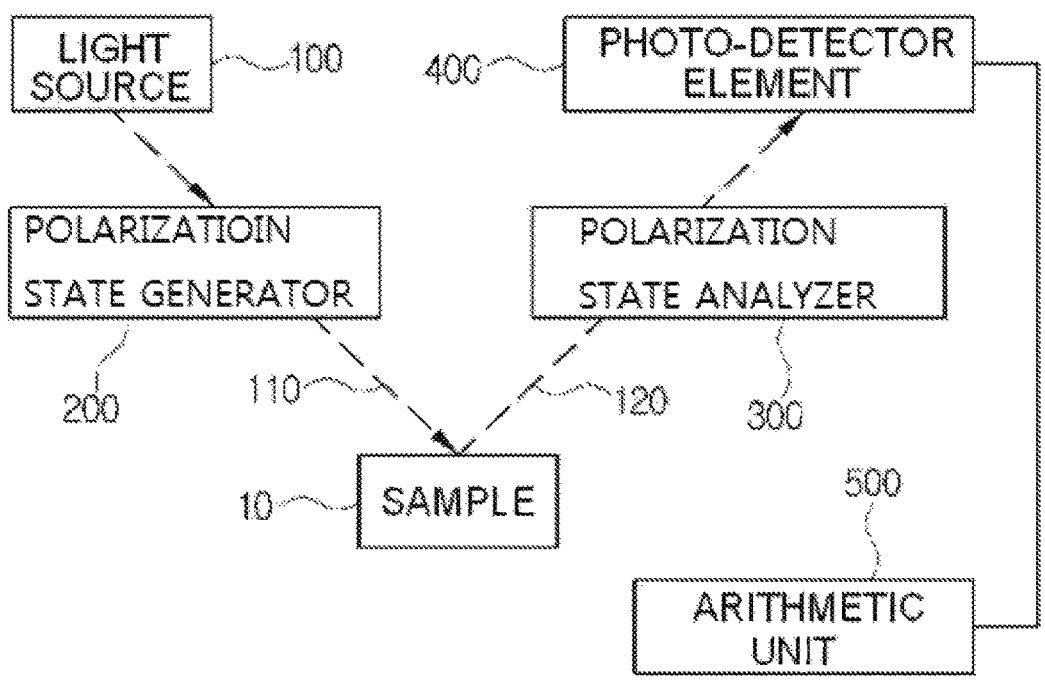
FIG. 1 is a block diagram of a rotating-element spectroscopic ellipsometer according to an exemplary embodiment of the present invention.

10: Sample
100: Light source
110: Incident light
120: Reflected light (or transmitted light)
200: Polarization state generator
300: Polarization state analyzer
400: Photodetector element
500: Arithmetic unit
S10: Input parameter
S30: Generate corrected Fourier coefficient function
S40: Generate Mueller matrix component vector for sample
S50: Generate ellipsometric parameter for sample
S60: Generate theoretical equation on sensitivity coefficient
S70: Generate theoretical equation on covariance
S80: Generate theoretical equation on standard deviation of ellipsometric parameters for sample
S90: Calculate optimum measurement condition

DETAILED DESCRIPTION OF EMBODIMENTS

Hereinafter, exemplary embodiments of the present invention will be described in more detail with reference to the accompanying drawings. Terms and words used in the present specification and claims are not to be construed as a general or dictionary meaning, but are to be construed as meaning and concepts meeting the technical ideas of the present invention based on a principle that the present inventors may appropriately define the concepts of terms in order to describe their inventions in best mode. Technical terms and scientific terms used in the present specification have the general meaning understood by those skilled in the art to which the present invention pertains unless otherwise defined, and a description for the known function and configuration obscuring the present invention will be omitted in the following description and the accompanying drawings. The accompanying drawings to be provided below are provided by way of example so that the idea of the present invention can be sufficiently transferred to those skilled in the art to which the present invention pertains. Therefore, the present invention is not limited to the accompanying drawings to be provided below, but may be implemented in other forms. In addition, like reference numerals denote like elements throughout the specification. In the drawings, it is to be noted that same reference numerals denote same elements.

FIG. 1 is a block diagram of a rotating-element spectroscopic ellipsometer according to an exemplary embodiment of the present invention and FIGS. 2 to 4 are flowcharts of a method for measurement precision prediction of a rotating-element spectroscopic ellipsometer according to an exemplary embodiment of the present invention.

As illustrated in FIG. 1, the rotating-element spectroscopic ellipsometer (RE-SE) according to the exemplary embodiment of the present invention includes a light source 100, a polarization state generator 200, a polarization state analyzer 300, a photodetector element 400, and an arithmetic unit 500, in which the polarization state generator 200 or the polarization state analyzer 300 includes a plurality of optical elements and the optical elements include constantly rotating elements rotating at a uniform velocity and scanning elements.

The light source 100 radiates an incident light 110 toward a sample 10.

The polarization state generator 200 is disposed between the light source 100 on a traveling path of the incident light 110 and the sample 10 and may control a polarized state of the incident light 110 radiated from the light source 100.

The polarization state analyzer 300 receives reflected light (or transmitted light) 120 having a changed polarization state while the incident light 100 is polarized by passing through the polarization state generator 200 and then reflected (or transmitted) by the sample 10 and analyzes a change in the polarization state of the reflected light (or transmitted light) 120.

The polarization state generator 200 or the polarization state analyzer 300 may be mounted with a plurality of rotatable elements.

The rotatable element is configured to include linear polarizers and compensators and is appropriately installed in the polarization state generator 200 and the polarization state analyzer 300 depending on the used kind of RE-SE. At least one of the rotatable elements is a constantly rotating element rotating at a uniform velocity and the rest rotatable elements includes the scanning elements moving at arbitrarily selected azimuths and stopping upon measurement.

The photodetector element 400 receives the reflected light (or the transmitted light) 120 passing through the polarization state analyzer 300 and measures irradiance of the incident light as an electrical signal of a voltage or a current.

When the constantly rotating element rotates at a uniform velocity at a rotating period T, J pulse signals may be generated at an equal interval of T/J from an optical encoder equipped in a rotating apparatus, each pulse signal may be transferred to the photodetector element 400 as an external trigger signal and an exposure may be measured whenever each pulse signal is transferred, a delay time $T_d$ after one trigger signal is transferred to the photodetector until the exposure measurement starts may occur during the measurement process by the photodetector element 400 for a rotating period T, the exposure may be measured for a set integration time $T_i$, the measured exposure data is changed into a digital signal to be stored, and when the storage ends, the exposure measurement waits until a subsequent trigger signal is arrived. In this case, the exposure is measured by the photodetector element 400.

In the rotating-element spectroscopic ellipsometer according to the present invention, a spectrometer, which is composed of one among photo-detectors formed of a charge coupled device (CCD) array, a complementary metal oxide semiconductor (CMOS) array, a photodiode array, or the like, and including a plurality of pixels arranged in a linear structure or a two-dimensional plane structure may be selected or a photo-detector formed of a photomultiplier tube (PMT), a photodiode, and the like, may be selected as the photo-detector. The photo-detector may include a cooling device selectively attached and used thereto in order to decrease a measurement error depending on a temperature.

The rotating-element spectroscopic ellipsometer according to the present invention may include a remote light source shielding device that is disposed behind the light source on a movement path of the light and may shield the light irradiated from the light source to the sample by a remote control.

In the rotating-element spectroscopic ellipsometer according to the present invention, the light source 100 may be a xenon lamp, a tungsten-halogen lamp, a deuterium lamp, a transfer of the light emitted from the lamp through an optical fiber, gas laser, a laser diode, or the like.

The arithmetic unit 500 calculates the measurement precision of the rotating-element spectroscopic ellipsometer (RE-SE) based on a theoretical equation on standard deviations of ellipsometric parameters for the sample.

Here, the ellipsometric parameters for the sample are at least any one selected from Mueller matrix components $M_{jk}$, normalized Mueller matrix components $m_{jk}=M_{jk}/M_{11}$, $[N_{SP}=-(m_{12}+m_{21})/2, C_{SP}=(m_{33}+m_{44})/2]$ when the rotatable elements all consist of a linear polarizer and are an isotropic sample, and $[N_{SP}=-(m_{12}+m_{21})/2, C_{SP}=(m_{33}+m_{44})/2, S_{SP}=(m_{34}-m_{43})/2]$ when at least one of the rotatable elements is configured of the compensator and are the isotroptic sample.

That is, the multi-channel RE-SE which is used for the measurement is selected, the sample which is used for the measurement precision assessment is selected, a measurement frequency N required for measurement, a measurement frequency J of exposure per one rotating period, a mechanical rotating period T of a constantly rotating element, a delay time $T_d$, and the system parameters of the integration time $T_i$, are determined, and an incident angle $\phi$, a measurement wavelength $\lambda$, and azimuths $\theta$ of the used scanning elements are selectively determined. Here, $\theta$ is differently set depending on a used kind of RE-SE. A rotating compensator design and a 3-polarizer design are configured to include an azimuth P of a scanning polarizer and an azimuth A of a scanning analyzer.

Further, it may be appreciated that the Mueller matrix components of the sample are given as a function of thicknesses of the thin film for each configuration layer in the sample and a refractive index thereof, a shape and a dimension of a nano pattern, the incident angle $\phi$, and the measurement wavelength $\lambda$. Here, as values of the refractive indexes of each layer, ones obtained by analyzing the RE-SE measurement value or ones obtained from related treatises may be used.

In this case, the arithmetic unit 500 may define Fourier coefficients of an irradiance waveform depending on the change in azimuth of the constantly rotating element as a function of constant values $\kappa$, $d_{12}$, $d_{13}$, $l_1$, and $l_2$ of common factors, optical properties (a refractive index, the thickness of the thin film, the shape and dimension of the nano pattern) of the sample, azimuths $\theta$ of the scanning elements, phase differences $\delta$ of the compensators, an incident angle $\phi$ and a measurement wavelength $\lambda$, derives a theoretical equation on Mueller matrix components of the sample from theoretical equations on the corrected Fourier coefficients, defines a theoretical equation on the ellipsometric parameters for the sample from the theoretical equation on the Mueller matrix components of the sample, defines theoretical equations on sensitivity coefficients from the theoretical equation on the ellipsometric parameters for the sample, defines a theoretical equation on the covariance for the corrected Fourier coefficients as a function of a measurement frequency N required for computation of the Fourier coefficient, a measurement frequency J of exposure per one rotating period, a mechanical rotating period T of the constantly rotating element, a delay time $T_d$, an integration time $T_i$, a scaling coefficient $\eta$, and the theoretical equations on the corrected Fourier coefficients, and calculates the theoretical equation on the standard deviations of the ellipsometric parameters for the sample from the theoretical equations on the covariance for the corrected Fourier coefficients and the theoretical equations on the sensitivity coefficients.

Further, the theoretical equation on the standard deviations of the ellipsometric parameters for the sample may depend on the following Equation.

$$\sigma(\langle Q \rangle) = \left[ \sum_{j=1}^{2N_{ho}+1} c_{Q,X_j}^2 \text{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \text{cov}(\langle X_j \rangle, \langle X_k \rangle) \right]^{1/2}$$

(In above Equation, $c_{Q,X_j} = \partial Q / \partial X_j$ is the sensitivity coefficient)

The theoretical equation on the standard deviations of the ellipsometric parameters for the sample will be described below.

Further, the rotatable elements all are configured of a linear polarizer and in the case of the isotropic sample, the ellipsometric parameters for the sample defined such as $N_{SP} = -(m_{12} + m_{21})/2$ and $C_{SP} = (m_{33} + m_{44})/2$ may be calculated from the plurality of corrected Fourier coefficients and physical properties for the sample of at least any one selected from interface characteristics, a thickness of a thin film, a complex refractive index, a nano shape, anisotropy characteristics, surface roughness, a composition ratio, and crystallinity may be analyzed based on the calculated ellipsometric parameters, and at least one of the rotatable elements is configured of compensator, and in the case of the isotropic sample, the ellipsometric parameters for the sample defined such as $N_{SP} = -(m_{12} + m_{21})/2$, $C_{SP} = (m_{33} + m_{44})/2$, $S_{SP} = (m_{34} - m_{43})/2$ may be calculated from the plurality of corrected Fourier coefficients and physical properties for the sample of at least any one selected from the interface characteristics, the thickness of the thin film, the complex refractive index, the nano shape, the anisotropy characteristics, the surface roughness, the composition ratio, and the crystallinity may be analyzed based on the calculated ellipsometric parameters, which may be utilized for a measurement equipment for a semiconductor device process, a measurement equipment for a flat panel display process, a solar cell measurement equipment, a thin film optical measurement equipment, a bio sensor, a gas sensor, or the like.

In the ideal RE-SE without an error, when a time is t, an irradiance value at a monochromatic wavelength measured by the photodetector element may be represented by the following general waveform Equation.

$$I(t) = I_0' + \sum_{n=1}^{N_{ho}} [A_n' \cos(n\omega t) + B_n' \sin(n\omega t)] \quad (1)$$

(In the above Equation, $I_0'$ represents a direct current (DC) component of the uncorrected Fourier coefficient, $A_n'$ and $B_n'$ represent the alternating current (AC) components of the uncorrected Fourier coefficient, $\omega$ ($=2\pi/T$) represents an angular frequency of the constantly rotating element rotating at a uniform velocity, and $N_{ho}$ represents an uppermost index value among nonzero AC components of the uncorrected Fourier coefficient)

In the case of a dual-rotating-element SE, two optical elements rotate at different uniform velocities and therefore the angular frequency $\omega$ may be defined by a ratio between the two angular frequencies.

The mainly used RE-SE may include all or some of the uncorrected Fourier coefficient components of an even number term but the special dual-rotating-element SE may also include components of an odd number term.

In the RE-SE, it is very important to accurately measure the uncorrected Fourier coefficients of the irradiance waveform using the photodetector element. In the state-of-the-art RE-SE, a charge coupled device array (CCD array) or a photodiode array (PD array) which may collect spectrum of the uncorrected Fourier coefficients as soon as possible for real-time measurement with high precision may be used as the photodetector. The CCD array or the photodiode array has relatively excellent measurement sensitivity against weak light, such that the defined light quantity may be measured within a shorter period of time. Each pixel or each binning pixel group of the CCD array or the photodiode array serves as one photodetector element. An output signal of the CCD array or the photodiode array is in proportion to the irradiance and the integration time and therefore is called an integral photodetector.

The data measurement process of the CCD array or the photodiode array may be classified into a frame acquisition process and a frame read process. One reference pulse is generated every measurement period, that is, per one rotation in a constantly rotating element system rotating at a uniform angular velocity, that is, every rotating period T of the constantly rotating element and J uniform clock pulses are generated at an equal interval of T/J. The reference pulse is a reference time informing the starting of the measurement by the ellipsometer and the uniform clock pulse is transferred as the external trigger for the data measurement by the CCD array or the photodiode array. After the uniform clock pulse is transferred to the CCD array or the photodiode array as the external trigger, the detailed process of the data measurement by the CCD array or the photodiode array for the period T is performed in a series of order as follows. If one photodetector element in each pixel or each binning pixel group of the CCD array or the photodiode array performs an exposure measurement process storing photons input for an integration time $T_i$ as photoelectrons after receiving the uniform clock pulse as the external trigger and having the time delay for $T_d$ prior to starting the exposure, and then performs the frame acquisition for converting the measured exposure into an electrical signal, one photodetector element waits to receive the next uniform clock pulse. Therefore, the measured exposure data are described by the integration of next waveform.

$$S_j = \int_{(j-1)T/J+T_d}^{(j-1)T/J+T_d+T_i} I(t)dt, (j=1, \ldots, J) \quad (2)$$

The exposure Equation measured based on the above Equations (1) and (2) is derived in the following form.

$$S_j = T_i I_0' + \sum_{n=1}^{N_{ho}} \frac{T_i}{\xi_n} \sin\xi_n \cos\left[\frac{2n\pi(j-1)}{J}\right]\left\{A_n' \cos\left[\xi_n\left(1+\frac{2T_d}{T_i}\right)\right] + B_n' \sin\left[\xi_n\left(1+\frac{2T_d}{T_i}\right)\right]\right\} - \sum_{n=1}^{N_{ho}} \frac{T_i}{\xi_n} \sin\xi_n \sin\left[\frac{2n\pi(j-1)}{J}\right]\left\{A_n' \sin\left[\xi_n\left(1+\frac{2T_d}{T_i}\right)\right] - B_n' \cos\left[\xi_n\left(1+\frac{2T_d}{T_i}\right)\right]\right\}. \quad (3)$$

(In the above Equation (3), $\xi_n = n\pi T_i/T$)

In the above Equation (3), J exposure sets measured for period T form a group of a linear Equation consisting of $2N_{ho}+1$ unknown Fourier coefficients of the above Equation (1), such that S may be simply expressed by S=ΞX'. Here, $S=(S_1, \ldots, S_J)^T$ representing the exposure and $X'=(I_0', A_1', B_1', \ldots, A_{N_{ho}}', B_{N_{ho}}')^T$ representing the uncorrected Fourier coefficients are a vector and Ξ is a coefficient matrix of J-by-$(2N_{ho}+1)$ dimensions.

If a least squares estimation is used when Ξ is not a singular matrix, a solution of calculating the uncorrected Fourier coefficient X' from the exposure S, like $X'=(\Xi^T\Xi)^{-1}\Xi^T S$ may be obtained.

If a discrete Fourier transform is applied to the exposures measured depending on the above Equation (3), the application result is the same as the result obtained by the least squares estimation but the expression method thereof may be simpler than the above Equation as follows.

$$\langle H_n^c \rangle + i\langle H_n^s \rangle = \frac{2}{NJ}\sum_{j=1}^{NJ} S_j \exp\left[i\frac{2n\pi(j-1)}{J}\right] \quad (4)$$

Here, $\langle H_n^c \rangle$ and $\langle H_n^s \rangle$ are a real valued function and angle brackets (<>) mean an average value for measurement values obtained by performing a total of N times measurements when the constantly rotating element performs measurement once for each mechanical rotation. Arranging the above Equation by substituting the above Equation (3) into the above Equation (4) and using orthogonality of a trigonometric function system, the average values of the uncorrected Fourier coefficients may be obtained as follows.

$$\langle I_0' \rangle = \frac{\langle H_0^c \rangle}{2T_i} \quad (5)$$

$$\langle A_n' \rangle = C_n^c \langle H_n^c \rangle - C_n^s \langle H_n^s \rangle, (n \geq 1) \quad (6)$$

$$\langle B_n' \rangle = C_n^c \langle H_n^s \rangle + C_n^s \langle H_n^c \rangle, (n \geq 1) \quad (7)$$

$$C_n^c = \frac{\xi_n}{T_i \sin\xi_n} \cos\left[\xi_n\left(1+\frac{2T_d}{T_i}\right)\right], (n \geq 1) \quad (8)$$

$$C_n^s = \frac{\xi_n}{T_i \sin\xi_n} \sin\left[\xi_n\left(1+\frac{2T_d}{T_i}\right)\right], (n \geq 1) \quad (9)$$

In the case of using the Equations (5) to (7), the results on how an effect of a measurement error by random noise is delivered from the exposure to the Fourier coefficients may be theoretically described.

Upon the actual measurement using the multi-channel RE-SE, statistical random noise is always included in the exposure value measured for the predetermined integration time by each pixel or each binning pixel group of the CCD array or the photodiode array. The random noise of the measured exposure consists of main factors of photon noise, dark noise, and read noise. The photon noise may be described by a method for stochastically calculating the number of photons incident on the photodetector element for the given integration time. Generally, for the more precision measurement under the measurement condition using the state-of-the-art RE-SE, attempts to increase a signal-to-noise ratio (SNR) if possible have been conducted. Therefore, in the case of increasing the irradiance to increase the SNR, the photon noise is increased in proportion to a square root of the irradiance but the dark noise and the read noise are independent of the irradiance and therefore the relative effect may be reduced. Therefore, under the general measurement condition using the state-of-the-art RE-SE, the dark noise and the read noise may be disregarded, compared to the photon noise. The measurement condition is called a photon noise limit. Additional factors of the random noise error occurring upon the measurement of the exposure may be induced by temporal instability of the irradiance, temporal change of background light, a change in velocity of the constantly rotating optical element, or the like, but the relative effect thereof may be small enough to be disregarded in the case of the high-performance RE-SE. It has been well known that the photon noise follows a Poisson distribution. According to the Poisson distribution, a dispersion of the number of photons detected by the photodetector element is equal to the average values of the number of photons. Therefore, a population dispersion of the exposure measured for the given integration time under the condition of the photon noise limit may be represented as follows.

$$\sigma^2(S_j) \approx \eta S_j \quad (10)$$

Here, $\eta = \epsilon_{PH}/(\eta_{QE} A_{PDE})$ represents the scaling coefficient and has the same unit as $S_j$ and $A_{PDE}$ and $\eta_{QE}$ each represent a measured effective area and a quantum efficiency of the photodetector element and $\epsilon_{PH}$ represents average energy of quasi-monochromatic photons incident on the photodetector element.

To obtain a theoretical equation of correlation coefficients with the standard deviations of the Fourier coefficients, we first use a new method for collecting data to derive the relational equation of covariance. The exposures measured for a different time are independent from each other and therefore the covariance therebetween is given as $\text{cov}(S_j, S_k) = \sigma^2(S_j)\delta_{jk}$. Here, $\delta_{jk}$ is Kronecker delta. Therefore, a sample covariance relational equation on the exposure may be obtained as follows.

$$\text{cov}\left(\sum_{j=1}^{NJ} c_j S_j, \sum_{k=1}^{NJ} c_k S_k\right) = \eta \sum_{j=1}^{NJ} c_j^2 S_j \quad (11)$$

Here, $c_j$ and $c_k$ are constants.

The covariance Equation on the sample mean of the uncorrected Fourier coefficients using the above Equation (11) is given as follows.

$$\text{cov}(\langle I_0' \rangle, \langle I_0' \rangle) = \sigma^2(\langle I_0' \rangle) = \frac{\eta}{NJT_i}\langle I_0' \rangle \quad (12)$$

$$\text{cov}(\langle A_n' \rangle, \langle A_n' \rangle) = \sigma^2(\langle A_n' \rangle) = \frac{2\eta\xi_n^2}{NJT_i\sin^2\xi_n}\left(\langle I_0' \rangle + \frac{\sin^2\xi_{2n}}{2\xi_{2n}}\langle A_{2n}' \rangle\right) \quad (13)$$

$$\text{cov}(\langle B_n' \rangle, \langle B_n' \rangle) = \sigma^2(\langle B_n' \rangle) = \frac{2\eta\xi_n^2}{NJT_i\sin^2\xi_n}\left(\langle I_0' \rangle - \frac{\sin^2\xi_{2n}}{2\xi_{2n}}\langle A_{2n}' \rangle\right) \quad (14)$$

$$\text{cov}(\langle I_0' \rangle, \langle A_n' \rangle) = \frac{\eta}{NJT_i}\langle A_n' \rangle \quad (15)$$

$$\text{cov}(\langle I_0' \rangle, \langle B_n' \rangle) = \frac{\eta}{NJT_i}\langle B_n' \rangle \quad (16)$$

$$\text{cov}(\langle A_n' \rangle, \langle A_m' \rangle) = \quad (17)$$
$$\frac{\eta m \xi_n}{NJT_i \sin\xi_n \sin\xi_m}\left(\frac{\sin\xi_{n+m}}{n+m}\langle A_{n+m}' \rangle + \frac{\sin\xi_{n-m}}{n-m}\langle A_{n-m}' \rangle\right),$$
$$(n \neq m),$$

$$\text{cov}(\langle B_n' \rangle, \langle B_m' \rangle) = \quad (18)$$
$$\frac{\eta m \xi_n}{NJT_i \sin\xi_n \sin\xi_m}\left(\frac{\sin\xi_{n-m}}{n-m}\langle A_{n-m}' \rangle - \frac{\sin\xi_{n+m}}{n+m}\langle A_{n+m}' \rangle\right),$$
$$(n \neq m),$$

$$\text{cov}(\langle A_n' \rangle, \langle B_m' \rangle) = \quad (19)$$
$$\begin{cases} \dfrac{\eta\xi_n}{NJT_i\tan\xi_n}\langle B_{2n}' \rangle, & (n=m) \\ \dfrac{\eta m \xi_n}{NJT_i\sin\xi_n\sin\xi_m}\left(\dfrac{\sin\xi_{n+m}}{n+m}\langle B_{n+m}' \rangle - \dfrac{\sin\xi_{n-m}}{n-m}\langle B_{n-m}' \rangle\right), & (n \neq m) \end{cases}$$

When a suffix nm of the uncorrected Fourier coefficients of Equations (17) to (19) is a negative number, the relational equations of $\langle A_{n-m}' \rangle = \langle A_{m-n}' \rangle$ and $\langle B_{n-m}' \rangle = -\langle B_{m-n}' \rangle$ derived from the above Equations (6) and (7) may be used. Further, a special relational equation of $\text{cov}(\langle A_{N_{ho}}' \rangle, \langle A_{N_{ho}}' \rangle) = \text{cov}(\langle B_{N_{ho}}' \rangle, \langle B_{N_{ho}}' \rangle)$ and $\text{cov}(\langle A_{N_{ho}}' \rangle, \langle B_{N_{ho}}' \rangle) = 0$ for the uppermost uncorrected Fourier coefficients may be obtained. When the integration time is much smaller than the measurement period, the results of Equations (12) to (14) are converged to the previous results obtained by the method for collecting data based on the discrete Fourier transform. The correlation coefficient for the uncorrected Fourier coefficient X' is given as follows.

$$r(\langle X_j' \rangle, \langle X_k' \rangle) = \frac{\text{cov}(\langle X_j' \rangle, \langle X_k' \rangle)}{\sigma(\langle X_j' \rangle)\sigma(\langle X_k' \rangle)} \quad (20)$$

Here, $\sigma(\langle X_j' \rangle) = \sqrt{\text{cov}(\langle X_j' \rangle, \langle X_j' \rangle)}$ is a standard deviation obtained by autocorrelation of the above Equations (12) to (14). When the average value of the uncorrected Fourier coefficients and system parameters of N, J, T, $T_d$, $T_i$, and $\eta$ are known, the covariance for the uncorrected Fourier coefficients and the correlation coefficients may be theoretically calculated using the above Equations (12) to (20).

In the general ellipsometer configuration, if the parallel light radiated from the light source passes through a polarization state generator (PSG) and is reflected (or transmitted) from the sample and then passes through a polarization state analyzer (PSA) to be incident on the photodetector element, the irradiance is converted into the electrical signal. The rotatable element used in the RE-SE is divided into a polarizer, an analyzer, and a compensator, which are differently disposed in the PSG and the PSA depending on a kind of RE-SE.

The rotatable elements may be made of a material having an anisotropic birefringence and the polarizer and the analyzer use a linear polarizer through which only the linearly polarized light may be transmitted in the defined direction and the compensator is an optical component made to have a phase difference of 90° ($\lambda/4$) between lights passing through a fast axis and a slow axis vertical thereto.

At least one of the rotatable elements in the RE-SE needs to rotate at a uniform velocity with a constant angular frequency and other rotatable elements each stop at the designated positions. The azimuths of the rotatable elements may be adjusted remotely by a hollow-shaft motor and when the azimuths of the rotatable elements are positioned at azimuth reference points of the hollow-shaft motor, that is, index origins, property axes of the rotatable elements may be at different positions.

To correctly perform the measurement, the azimuth positions of the property axes of the rotatable elements each need to be found from an axis parallel to the incident surface, that is, a real origin. When using a calibration technique already well known, the azimuth positions of the property axes of the optical elements may be each found at a real origin coordinate system. Therefore, the above Equation (1) is transformed on the real origin coordinate system and thus is given as follows.

$$I(\theta_r) = I_0 + \sum_{n=1}^{N_{ho}} [A_n \cos(n\theta_r) + B_n \sin(n\theta_r)] \quad (21)$$

In the above Equation (21), $\theta_r$ represents the azimuth of the property axis of the constantly rotating element measured for the real origin, $I_0$ represents the direct current (DC) component of the corrected Fourier coefficient, $A_n$ and $B_n$ are the alternating current (AC) components of the corrected Fourier coefficient. In the above Equation (21), when the azimuth is expressed by $\omega t = \theta_r + \theta_{r0}$, $-\theta_{r0}$ becomes a value of $\theta_r$ when $t=0$ and the relational equation between the uncorrected and corrected Fourier coefficients is given as follows from an identity relational equation between the uncorrected (primed) Fourier coefficients and the corrected (unprimed) Fourier coefficients.

$$I_0 = I_0', \tag{22}$$

$$A_n = A_n' \cos(n\theta_{r0}) + B_n' \sin(n\theta_{r0}), \tag{23}$$

$$B_n = -A_n' \sin(n\theta_{r0}) + B_n' \cos(n\theta_{r0}). \tag{24}$$

In the case of the state-of-the-art RE-SE, since a dispersion value of $\theta_{r0}$ depending on the temporal change of the angular frequency of the constantly rotating element is very small, if the error therefore is disregarded, the covariance function between the corrected Fourier coefficients X is given as $\text{cov}(\langle X_j \rangle, \langle X_k \rangle) \cong \text{cov}(\langle X_j' \rangle, \langle X_k' \rangle)$ from the above Equations (22) to (24). Therefore, the covariance function between the corrected Fourier coefficients is given as Equation having the same type as the case in which the uncorrected Fourier coefficients in the above Equations (12) to (19) are replaced by the corrected Fourier coefficients.

In the ellipsometer, a data reduction function is used to extract the ellipsometric parameters for the sample from the corrected Fourier coefficients and therefore it is very important to find out the method for reducing data suitable for the used RE-SE. According to a Stokes representation, a Stokes vector of a light wave just before impinging on the PSG is $S^{(LS)} = (L_0, L_1, L_2, L_3)^T$, the Mueller matrix of the sample is expressed by $M^{(SP)} = (M_{jk})_{4 \times 4}$, the Mueller matrixes of the PSG and the PSA are each expressed by $T_{PSG}M^{(PSG)}$ and $T_{PSA}M^{(PSA)}$. Here, $T_{PSG}$ and $T_{PSA}$ each are a transmission coefficient of the PSG and the PSA, $M^{(DOS)} = (D_{jk})_{4 \times 4}$ is the Mueller matrix of a detector optic system (DOS) disposed between the PSA and the photodetector element, and finally, $S^{(PDE)} = (S_0^{(PDE)}, S_1^{(PDE)}, S_2^{(PDE)}, S_3^{(PDE)})^T$ is the Stokes vector of the light wave measured by the photodetector element. The positions of the azimuths of the property axes of the polarizer, the analyzer, and the compensator which are disposed in the PSG and the PSA are each expressed by P, A, and C at the real origin coordinate system and the changes in the azimuths thereof are each described by the Mueller matrixes for the rotation of the coordinate system.

The Stokes vector for the monochromatic light wave measured by the photodetector element (PDE) may be described as follows.

$$S^{(PDE)} = \frac{c\varepsilon_0}{2} \eta_{QE} A_{PDE} T_{PSA} T_{PSG} M^{(DOS)} M^{(PSA)} M^{(SP)} M^{(PSG)} S^{(LS)} \tag{25}$$

In the above Equation (25), c is a velocity of light under vacuum, $\varepsilon_0$ is permittivity of vacuum, $\eta_{QE}$ is quantum efficiency of the PDE, and $A_{PDE}$ is effective area of the PDE. The solutions for the corrected Fourier coefficients obtained by the relational equation of $I(\theta_r) = S_0^{(PDE)}$ are given in a simultaneous linear Equation form for the Mueller matrix components of the sample. To more simply represent the simultaneous linear Equation, a vector having the Mueller matrix components for the sample such as $V^{(SP)} = (M_{11}, \ldots, M_{1v}, \ldots, M_{u1}, \ldots, M_{uv})^T$ is introduced. Here, u and v are integers differently given depending on a kind of the used RE-SE and the superscript T is a sign representing a transposed matrix performing a transposition in a matrix. Therefore, the corrected Fourier coefficients are given by a scalar product as follows.

$$I_0 = \gamma \sum_{j=1}^{u} \sum_{k=1}^{v} i_{0,jk} M_{jk} = \gamma i_0 \cdot V^{(SP)}, \tag{26}$$

$$A_n = \gamma \sum_{j=1}^{u} \sum_{k=1}^{v} a_{n,jk} M_{jk} = \gamma a_n \cdot V^{(SP)}, \tag{27}$$

$$B_n = \gamma \sum_{j=1}^{u} \sum_{k=1}^{v} b_{n,jk} M_{jk} = \gamma b_n \cdot V^{(SP)}. \tag{28}$$

Here, $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$, $b_2 = (\partial B_n/\partial M_{11}, \ldots, \partial B_2/\partial M_{1v}, \ldots, \partial B_n/\partial M_{u1}, \ldots, \partial B_n/\partial M_{uv})/\gamma$ are a function of only the azimuths $\theta$ of the scanning elements but if the compensators are included, are a function in which the azimuths $\theta$ and the phase differences $\delta$ of the compensators are further included and are described as a row vector. In the case of the RE-SEs in which the scanning polarizer is installed at a foremost part toward the light source unit within the PSG and the scanning analyzer is installed at the nearest position to the photodetector within the PSA, $\gamma$ is a common factor related to the irradiance and the polarization characteristics of the light source, an effective detection area and the quantum efficiency of the photodetector element, polarization dependence characteristics of the DOS, and the transmittances of the optical elements used in the RE-SE and may be given as follows.

$$\gamma = \kappa(1 + d_{12} \cos 2A + d_{13} \sin 2A)(1 + l_1 \cos 2P + l_2 \sin 2P) \tag{29}$$

Here, $\kappa = c\varepsilon_0 \eta_{QE} A_{PDE} T_{PSA} T_{PSG} D_{11} L_0/2$, $d_{12(13)} = D_{12(13)}/D_{11}$, and $l_{1(2)} = L_{1(2)}/L_0$.

The solution of the simultaneous linear equation depending on the total number of linear equations used in a data reduction is given in a unique or overdetermined form. The present research introduces a generalized data reduction method which may be applied to all the types of RE-SEs and may obtain the ellipsometric parameters for the sample from all the corrected Fourier coefficients. If the vector of the corrected Fourier coefficients is expressed by $X = (I_0, A_1, B_1, A_2, B_2, \ldots, A_{N_{ho}}, B_{N_{ho}})^T$ and the $(2N_{ho}+1)$-by-uv coefficient matrix consisting of the row vector as the component is expressed by $\Omega = \gamma(i_0, a_1, b_1, a_2, b_2, \ldots, a_{N_{ho}}, b_{N_{ho}})^T$, the above Equations (26) to (28) may be represented by $X = \Omega V^{(SP)}$. When a matrix rank of $\Omega$ is equal to or larger than a total number of unknown matrix elements at the $M^{(SP)}$, the solution of the vector for the Mueller matrix component for the sample is given as follows.

$$V^{(SP)} = (\Omega^T \Omega)^{-1} \Omega^T X \tag{30}$$

An object of the present research is to develop a general theory model of uncertainty assessment which may be applied to various kinds of multi-channel RE-SEs. By the above Equations (12) to (19), it is possible to obtain the covariance equation between the corrected and uncorrected Fourier coefficients describing the waveform of the irradiance which may not be implemented in the past and derive the theory equation (Equation (20)) for the standard deviations and the correlation coefficients for the corrected and uncorrected Fourier coefficients therefrom. Meanwhile, the theoretical equation on calculating the data reduction, that is, the ellipsometric parameters which are the final measurement value of the ellipsometer for the sample from the corrected Fourier coefficients has different forms depending on the kind of RE-SEs, and therefore the transfer value of the measurement error is also different depending on the selected data reduction method. Therefore, the theoretical equation on the standard deviations for the measurement of the ellipsometric parameters may be obtained by finding out the data reduction method which may be applied to various kinds of RE-SEs and using it. In summary, the theoretical equation on the standard deviations and the correlation coefficients for the corrected Fourier coefficients are found by a Fourier analysis method, the sensitivity coefficient is derived from the theoretical equations of the ellipsometric parameters for the sample obtained by using a new data reduction method, and the theoretical equation on the standard deviation of the ellipsometric parameters for the sample, that is, the measurement precision may be obtained from the standard deviations and the correlation coefficients for the corrected Fourier coefficients and the sensitivity coefficient.

Therefore, if a value of $\gamma$ for each wavelength is obtained from a measurement result using a reference sample in which optical properties are well known or a measurement result on the straight line without a sample, the Mueller matrix components of the sample may be directly calculated from the values of the corrected Fourier coefficients using the above Equation (30). Even if the value of $\gamma$ is unknown, the measurement values of the ellipsometric parameters for the sample defined as a normalized Mueller matrix components like $m_{jk}=M_{jk}/M_{11}$ may be obtained. In the case of the isotropic sample, generally, the ellipsometric parameters for the sample defined as $N_{SP}=-(m_{12}+m_{21})/2$, $C_{SP}=(m_{33}+m_{44})/2$, and $S_{SP}=(m_{34}-m_{43})/2$ have been mainly used. If the compensator is not included in the used RE-SE, an $S_{SP}$ component among the ellipsometric parameters may not be measured. If Q(X) is one selected from the ellipsometric parameters for the sample, the standard deviation therefor is given as follows.

$$\sigma(\langle Q \rangle) = \left[ \sum_{j=1}^{2N_{ho}+1} c_{Q,X_j}^2 \text{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \text{cov}(\langle X_j \rangle, \langle X_k \rangle) \right]^{1/2} \quad (31)$$

(In above Equation (31), $C_{Q,X_j}=\partial Q/\partial X_j$ is the sensitivity coefficient)

As illustrated in FIG. 2, the method for measurement precision prediction of a rotating-element spectroscopic ellipsometer for calculating the measurement precision of the rotating-element spectroscopic ellipsometer including the light source 100, the polarization state generator 200, the polarization state analyzer 300, the photodetector element 400, and the arithmetic unit 500, in which the polarization state generator 200 or the polarization state analyzer 300 includes a plurality of rotatable elements and the rotatable elements include constantly rotating elements rotating at a uniform velocity and scanning elements, the method includes generating a function of corrected Fourier coefficient (S30), generating a Mueller matrix component vector for a sample (S40), generating an ellipsometric parameter for a sample (S50), generating a theoretical equation on a sensitivity coefficient (S60), generating a theoretical equation on a covariance (S70), and generating a theoretical equation on standard deviations of ellipsometric parameters for the sample (S80).

In the generating of the function of the corrected Fourier coefficient (S30), a function of the corrected Fourier coefficients X consisting of constant values $\kappa$, $d_{12}$, $d_{13}$, $l_1$, and $l_2$ of common factors, optical properties (a refractive index, a thickness of a thin film, a shape and a dimension of a nano pattern) of a sample, azimuths $\theta$ of the scanning elements, phase differences $\delta$ of compensators, an incident angle $\phi$, and a measurement wavelength $\lambda$ is generated.

In this case, the function of the corrected Fourier coefficients X in the generating of the function of the corrected Fourier coefficient (S30) depends on the following Equation.

$$I_0 = \gamma \sum_{j=1}^{u} \sum_{k=1}^{v} i_{0,jk} M_{jk} = \gamma i_0 \cdot V^{(SP)}$$

$$A_n = \gamma \sum_{j=1}^{u} \sum_{k=1}^{v} a_{n,jk} M_{jk} = \gamma a_n \cdot V^{(SP)}$$

$$B_n = \gamma \sum_{j=1}^{u} \sum_{k=1}^{v} b_{n,jk} M_{jk} = \gamma b_n \cdot V^{(SP)}$$

Here, $\gamma=\kappa(1+d_{12}\cos 2A+d_{13}\sin 2A)(1+l_1\cos 2P+l_2\sin 2P)$, $\kappa=c\epsilon_0\eta_{QE}A_{PDE}T_{PSA}T_{PSG}D_{11}L_0/2$, $d_{12(13)}=D_{12(13)}/D_{11}, l_{1(2)}=L_{1(2)}/L_0$.

In other words, by using the above Equations (26) to (28), the corrected Fourier coefficients X are obtained based on a function of constant values $\kappa$, $d_{12}$, $d_{13}$, $l_1$, and $l_2$ of common factors, optical properties (a refractive index, the thickness of the thin film, the shape and dimension of the nano pattern) of the sample, azimuths $\theta$ of the scanning elements, phase differences $\delta$ of the compensators, an incident angle $\phi$, and a measurement wavelength $\lambda$.

In the generating of the Mueller matrix component vector for a sample (S40), the Mueller matrix component vector $V^{(SP)}(X)$ of the sample consisting of the function of the corrected Fourier coefficients X is generated.

In this case, the Mueller matrix component vector $V^{(SP)}(X)$ of the sample in the generating of the Mueller matrix component vector for a sample (S40) depends on the following Equation.

$$V^{(SP)}=(\Omega^T\Omega)^{-1}\Omega^T X$$

Here, $\Omega = \gamma(i_0, a_1, b_1, a_2, b_2, \ldots, a_{N_{ho}}, b_{N_{ho}})^T$, $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$, $b_n = (\partial B_n/\partial M_{11}, \ldots, \partial B_n/\partial M_{1v}, \ldots, \partial B_n/\partial M_{u1}, \ldots, \partial B_n/\partial M_{uv})/\gamma$, In other words, by the above Equation (30), the Mueller matrix component vector $V^{(SP)}(X)$ of the sample is obtained based on the corrected Fourier coefficients X, the constant values $\kappa$, $d_{12}$, $d_{13}$, $l_1$, and $l_2$ of the common factors, the azimuths $\theta$ of the scanning elements, and the phase differences $\delta$ of the compensators.

In the generating of the ellipsometric parameter for the sample (S50), the ellipsometric parameter Q(X) of the sample consisting of the function of the corrected Fourier coefficients X is obtained from the Mueller matrix components obtained in the generating of the Mueller matrix component vector (S40).

In other words, the ellipsometric parameter Q(X) of the sample is obtained based on the function of the corrected Fourier coefficients X from the Mueller matrix components obtained in the generating of the Mueller matrix component vector $V^{(SP)}(X)$ of the sample (S40).

In the generating of the theoretical equation on a sensitivity coefficient (S60), the theoretical equation on the sensitivity coefficient is generated using the function of the corrected Fourier coefficients X using a partial derivative of $c_{Q,X_j} = \partial Q/\partial X_j$ from the ellipsometric parameter Q(X) of the sample in the generating of the ellipsometric parameter (S50).

In other words, the theoretical equation on the sensitivity coefficient is obtained based on the function of the corrected Fourier coefficients X using the partial derivative of $c_{Q,X_j} = \partial Q/\partial X_j$ from the ellipsometric parameter Q(X) of the sample in the generating of the theoretical equation on a sensitivity coefficient (S60).

In the generating of the theoretical equation on the covariance (S70), the theoretical equation on the covariance of the corrected Fourier coefficients X is generated.

In other words, the theoretical equation on the covariance of the corrected Fourier coefficients X is obtained from the covariance equations (12) to (20) on the uncorrected Fourier coefficients X: using the following relational equation $cov(\langle X_j \rangle, \langle X_k \rangle) \cong cov(\langle X_j' \rangle, \langle X_k' \rangle)$.

In this case, the theoretical equation on the covariance of the uncorrected Fourier coefficient X' in the generating of the theoretical equation on the covariance (S70) depends on the following Equation.

$$cov(\langle I_0' \rangle, \langle I_0' \rangle) = \sigma^2(\langle I_0' \rangle) = \frac{\eta}{NJT_i}\langle I_0' \rangle,$$

$$cov(\langle A_n' \rangle, \langle A_n' \rangle) = \sigma^2(\langle A_n' \rangle) = \frac{2\eta\xi_n^2}{NJT_i\sin^2\xi_n}\left(\langle I_0' \rangle + \frac{\sin\xi_{2n}}{2\xi_{2n}}\langle A_{2n}' \rangle\right),$$

$$cov(\langle B_n' \rangle, \langle B_n' \rangle) = \sigma^2(\langle B_n' \rangle) = \frac{2\eta\xi_n^2}{NJT_i\sin^2\xi_n}\left(\langle I_0' \rangle - \frac{\sin\xi_{2n}}{2\xi_{2n}}\langle A_{2n}' \rangle\right),$$

$$cov(\langle I_0' \rangle, \langle A_n' \rangle) = \frac{\eta}{NJT_i}\langle A_n' \rangle,$$

$$cov(\langle I_0' \rangle, \langle B_n' \rangle) = \frac{\eta}{NJT_i}\langle B_n' \rangle,$$

$$cov(\langle A_n' \rangle, \langle A_m' \rangle) =$$

$$\frac{\eta m \xi_n}{NJT_i \sin\xi_n \sin\xi_m}\left(\frac{\sin\xi_{n+m}}{n+m}\langle A_{n+m}' \rangle + \frac{\sin\xi_{n-m}}{n-m}\langle A_{n-m}' \rangle\right), \quad (n \neq m),$$

$$cov(\langle B_n' \rangle, \langle B_m' \rangle) =$$

$$\frac{\eta m \xi_n}{NJT_i \sin\xi_n \sin\xi_m}\left(\frac{\sin\xi_{n-m}}{n-m}\langle A_{n-m}' \rangle - \frac{\sin\xi_{n+m}}{n+m}\langle A_{n+m}' \rangle\right), \quad (n \neq m),$$

$$cov(\langle A_n' \rangle, \langle B_m' \rangle) =$$

$$\begin{cases} \frac{\eta \xi_n}{NJT_i \tan\xi_n}\langle B_{2n}' \rangle, & (n = m), \\ \frac{\eta m \xi_n}{NJT_i \sin\xi_n \sin\xi_m}\left(\frac{\sin\xi_{n+m}}{n+m}\langle B_{n+m}' \rangle - \frac{\sin\xi_{n-m}}{n-m}\langle B_{n-m}' \rangle\right), & (n \neq m), \end{cases}$$

In above Equations, $\xi_n = n\pi T_i/T$.

In the generating of the theoretical equation on the standard deviations of the ellipsometric parameters for the sample (S80), the results of the generating of the theoretical equation on the sensitivity coefficient (S60) and the generating of the theoretical equation on the covariance (70) are substituted into the following Equation.

$$\sigma(\langle Q \rangle) = \left[\sum_{j=1}^{2N_{ho}+1} c_{Q,X_j}^2 cov(\langle X_j \rangle, \langle X_j \rangle) + 2\sum_{j=1}^{2N_{ho}}\sum_{k=j+1}^{2N_{ho}+1} c_{Q,X_j} c_{Q,X_k} cov(\langle X_j \rangle, \langle X_j \rangle)\right]^{1/2}$$

(In the above Equation, the theoretical equation on the corrected Fourier coefficients X may be obtained from the generating of the function of the corrected Fourier coefficient (S30)) to generate the theoretical equation $\sigma(\langle Q \rangle)$ on the standard deviations of the ellipsometric parameter Q of the sample consisting of the function of the measurement frequency N required for computation of the Fourier coefficient, a measurement frequency J of exposure per one rotating period, a mechanical rotating period T of the constantly rotating element, a delay time $T_d$, an integration time $T_i$, a scaling coefficient η, and the theoretical equations on the corrected Fourier coefficients X.

In other words, if the results of the generating of the theoretical equation on the sensitivity coefficient (S60) and the generating of the theoretical equation on a covariance (S70) are substituted into the above Equation (31), the theoretical equation $\sigma(\langle Q \rangle)$ on the standard deviations of the ellipsometric parameter Q of the sample is obtained based on the function of the system parameters of N, J, T, $T_d$, and $T_i$ and the corrected Fourier coefficient X. Here, the theoretical equation on the Fourier coefficients X may be obtained based on the function of the constant values κ, $d_{12}$, $d_{13}$, $l_1$, and $l_2$ of the common factors, the optical properties (a refractive index, the thickness of the thin film, the shape and dimension of the nano pattern) of the sample, the azimuths θ of the scanning elements, the phase differences δ of the compensators, the incident angle φ, and the measurement wavelength λ by using the above Equations (25) to (28).

By this, a theoretical model equation (the theoretical equation $\sigma(\langle Q \rangle)$ on the standard deviations of the ellipsometric parameter Q of the sample) which may be applied to various kinds of multi-channel RE-SEs and may determine the measurement limit may be generated.

As illustrated in FIG. 3, the method for measurement precision prediction of a rotating-element spectroscopic ellipsometer according to the exemplary embodiment of the present invention may further include inputting parameters (S10) prior to the generating of the function of corrected Fourier coefficient (S30).

In the inputting of the parameters (S10), the constant values κ, $d_{12}$, $d_{13}$, $l_1$, and $l_2$ of the common factors, the optical properties (a refractive index, the thickness of the thin film, the shape and dimension of the nano pattern) of the sample, a measurement frequency N required for computation of the Fourier coefficient, a measurement frequency J of exposure per one rotating period, a mechanical rotating period T of the constantly rotating element, a delay time $T_d$, an integration time $T_i$, the incident angle φ, the measurement wavelength λ, the azimuths θ of the used scanning elements, and the phase difference δ of the compensators are input.

As illustrated in FIG. 4, the method for measurement precision prediction of a rotating-element spectroscopic ellipsometer according to the exemplary embodiment of the present invention may further include calculating an optimum measurement condition for finding out a position of the azimuth θ of the scanning elements or the incidence angle φ having a minimum value of Z in a measurement precision assessment function Z depending on the following Equation, when the number of measurement wavelengths 2 is $N_\lambda$ and the number of kinds of ellipsometric parameters $Q_k(\lambda_j)$ of the sample is $N_Q$ (S90), after the generating of the theoretical equation on the standard deviations of the ellipsometric parameters for the sample (S80).

$$Z = \sqrt{\frac{1}{N_\lambda N_Q} \sum_{j=1}^{N_\lambda} \sum_{k=1}^{N_Q} \sigma^2(\langle Q_k(\lambda_j)\rangle)}$$

In other words, by calculating the azimuth θ of the scanning elements or the incidence angle φ in which the value of the measurement precision assessment function Z in the calculating of the optimum measurement condition (S90) is minimum, the optimum measurement condition for any sample may be found using the multi-channel RE-SE.

That is, a value of η and values of κ, $d_{12}$, $d_{13}$, $l_1$, and $l_2$ at γ are determined from the measured data for a plurality of selected azimuths of the scanning elements and values of η, κ, $d_{12}$, $d_{13}$, $l_1$, and $l_2$ are substituted into the function of σ(⟨Q⟩) derived from the above Equation (31), that is, the theoretical equation σ(⟨$Q_k(\lambda_j)$⟩) on the standard deviations of the ellipsometric parameter $Q_k(\lambda_j)$ of the sample to calculate the optimization condition of the measurement if a position of the azimuth θ of the scanning elements or the incidence angle φ in which the value of the measurement precision assessment function Z is minimum is found when the number of measurement wavelength λ is $N_\lambda$ and the number of kinds of ellipsometric parameters Q is $N_Q$.

An example of the method for finding out the values of η, κ, $d_{12}$, $d_{13}$, $l_1$, and $l_2$ calculated as follows in the case of the rotating-compensator design and the three-polarizer design will be described.

First, the scaling coefficient is given like η=$NJT_i\sigma^2$(⟨$I_0$⟩)/⟨$I_0$⟩ from the above Equation (12) and therefore the values η for each wavelength are each obtained by substituting experiment values of an average value ⟨$I_0$⟩ and a standard deviation σ(⟨$I_0$⟩) for the direct current component of the Fourier coefficient measured for any sample. The Mueller matrix components $M_{jk}$ for the selected sample are created as the function of the optical properties (a refractive index, the thickness of the thin film, the shape and dimension of the nano pattern) of the sample, the incident angle φ, and the measurement wavelength λ and then are substituted into the above Equation (26), and the experiment values for the corrected Fourier coefficient components for the plurality of selected azimuths P for the scanning polarizer are measured and the values of $l_1$ and $l_2$ in the above Equation (29) are obtained for each wavelength from the measurement value and the fitting of the least squares estimation using the theoretical equation of the above equation (26). Next, the experiment values for the corrected Fourier coefficient components for the plurality of selected azimuths A for the scanning analyzer are measured and the values of κ, $d_{12}$, and $d_{13}$ in the above Equation (29) are obtained for each wavelength from the measurement value and the fitting of the least squares estimation using the theoretical equation of the above equation (26).

Hereinabove, the method for measurement precision prediction of a rotating-element spectroscopic ellipsometer according to the exemplary embodiment of the present invention is described, but the computer-readable recording medium stored with the program for implementing the method for measurement precision prediction of a rotating-element spectroscopic ellipsometer and the program stored in the computer-readable recording medium for implementing the method for measurement precision prediction of a rotating-element spectroscopic ellipsometer may also be implemented.

That is, the programs of commands for implementing the method for measurement precision prediction of a rotating-element spectroscopic ellipsometer as described above may be variously implemented and thus it may be easily understood by those skilled in the art in that it may be included in the computer-readable recording medium. Exemplary embodiments of the present invention may be implemented in a form of program commands that may be executed through various computer means and may be recorded in a computer-readable recording medium. The computer-readable recording medium may include a program command, a data file, a data structure or the like, alone or a combination thereof. The program command recorded in the computer-readable recording medium may be designed and configured especially for the present invention, or may be known to those skilled in a field of computer software. An example of the computer readable recording medium may include magnetic media such as hard disk, floppy disk, magnetic tape, and the like, optical media such as CD-ROM, DVD, and the like, magneto-optical media such as floptical disk, and hardware devices specially configured to store and perform program commands such as ROM, RAM, flash memory, USB memory, and the like. Meanwhile, the computer readable recording medium may also be a transmission medium such as light including a carrier wave transmitting a signal specifying a program command, a data structure, or the like, a metal line, a waveguide, or the like. Examples of the program commands may include a high-level language code capable of being executed by a computer using an interpreter, or the like, as well as a machine language code made by a compiler. The hardware device may be constituted to be operated as one or more software modules in order to perform the action according to the present invention, and vice versa.

According to the rotating-element spectroscopic ellipsometer and the method for measurement precision prediction of a rotating-element spectroscopic ellipsometer, the recording medium storing program for executing the same, and the computer program stored in a medium for executing the same according to the exemplary embodiments of the present invention, the following effects are obtained.

It is possible to assess the measurement uncertainty of various kinds of multi-channel RE-SEs based on the fact that the theoretical equation on the standard deviations of the ellipsometric parameters for the sample may be applied to all the kinds of rotating-element spectroscopic ellipsometers.

It is possible to obtain the covariance equation between the Fourier coefficients describing an irradiance waveform which may not be implemented in the past.

It is possible to derive the theoretical equation on the standard deviations and the correlation coefficients for the Fourier coefficients from the covariance between the Fourier coefficients describing the irradiance waveform.

It is possible to find out the optimum measurement conditions of the rotating-element spectroscopic ellipsometer for any sample using the measurement precision assessment function and perform the comparison assessment for the measurement precision between different kinds of RE-SEs.

The present invention is not limited to the above-mentioned exemplary embodiments, and may be variously applied, and may be variously modified without departing from the gist of the present invention claimed in the claims.

What is claimed is:

1. A rotating-element spectroscopic ellipsometer, comprising:
   a light source radiating an incident light toward a sample;
   a polarization state generator disposed between the light source on a traveling path of the incident light and the sample and controlling a polarized state of the incident light radiated from the light source;
   a polarization state analyzer receiving reflected light or transmitted light having a changed polarization state while the incident light is polarized by passing through the polarization state generator and then reflected or transmitted by the sample and analyzing a change in the polarization state of the reflected light or transmitted light;
   a photodetector element receiving the reflected light or the transmitted light passing through the polarization state analyzer and measuring irradiance of the incident light with an electrical signal of a voltage or a current; and
   a processor operable for calculating measurement precision of the rotating-element spectroscopic ellipsometer based on a theoretical equation on standard deviations of ellipsometric parameters for the sample,
   wherein the theoretical equation on the standard deviations $\sigma(\langle Q \rangle)$ of the ellipsometric parameters Q for the sample depends on the following equation $$\sigma(\langle Q \rangle) = \left[ \sum_{j=1}^{2N_{ho}+1} c_{Q,X_j}^2 \text{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \text{cov}(\langle X_j \rangle, \langle X_k \rangle) \right]^{1/2},$$

wherein, represent $X=(X_j)_{(2N_{ho}+1) \times 1}$ represent a vector of the corrected Fourier coefficients, $C_{Q,X_j} = \partial Q/\partial X_j$ represents a sensitivity coefficient, $\text{cov}(\langle X_j \rangle, \langle X_k \rangle)$ represents a covariance between the corrected Fourier coefficients, angle brackets (< >) represent a sample mean, and $N_{ho}$ represents an uppermost index value among nonzero alternating current (AC) components of the corrected Fourier coefficient, and
   wherein a plurality of rotatable elements are disposed in the polarization state generator or the polarization state analyzer and the rotatable element includes a constantly rotating element rotating at a uniform velocity and a scanning element.

2. The rotating-element spectroscopic ellipsometer of claim 1, wherein the ellipsometric parameters for the isotropic sample are at least any one selected from Mueller matrix components $M_{jk}$, normalized Mueller matrix components $m_{jk}=M_{jk}/M_{11}$, $[N_{SP}=-(m_{12}+m_{21})/2, C_{SP}=(m_{33}+m_{44})/2]$ when the rotatable elements all consist of linear polarizers, and $[N_{SP}=-(m_{12}+m_{21})/2, C_{SP}=(m_{33}+m_{44})/2, S_{SP}=(m_{34}-m_{43})/2]$ when the rotatable elements are configured of linear polarizers and compensators.

3. The rotating-element spectroscopic ellipsometer of claim 1, wherein the arithmetic unit defines Fourier coefficients of an irradiance waveform depending on the change in azimuth of the constantly rotating element as a function of constant values $\kappa$, $d_{12}$, $d_{13}$, $l_1$, and $l_2$ of common factors, optical properties (a refractive index, a thickness of a thin film, a shape and dimension of a nano pattern) of the sample, azimuths $\theta$ of the scanning elements, phase differences $\delta$ of compensators, an incident angle $\phi$, and a measurement wavelength $\lambda$, derives a theoretical equation on Mueller matrix components of the sample from theoretical equations on the Fourier coefficients, defines a theoretical equation on the ellipsometric parameters for the sample from the theoretical equation on the Mueller matrix components of the sample, defines theoretical equations on sensitivity coefficients from the theoretical equation on the ellipsometric parameters for the sample, defines a theoretical equation on a covariance for the Fourier coefficients as a function of a measurement frequency N required for computation of the Fourier coefficient, a measurement frequency J of exposure per one rotating period, a mechanical rotating period T of the constantly rotating element, a delay time $T_d$, an integration time $T_i$, a scaling coefficient $\eta$, and the theoretical equations on the Fourier coefficients, and calculates the theoretical equation on the standard deviations of the ellipsometric parameters for the sample from the theoretical equations on the covariance for the Fourier coefficients and the theoretical equations on the sensitivity coefficients.

4. The rotating-element spectroscopic ellipsometer of claim 2, wherein physical properties for the sample of at least any one of interface characteristics, the thickness of the thin film, a complex refractive index, a nano shape, anisotropy characteristics, surface roughness, a composition ratio, and crystallinity from the selected ellipsometric parameters for the sample are analyzed.

5. A method for measurement precision prediction of a rotating-element spectroscopic ellipsometer for calculating the measurement precision of the rotating-element spectroscopic ellipsometer including a light source, a polarization state generator, a polarization state analyzer, a photodetector element, and an arithmetic unit, in which the polarization state generator or the polarization state analyzer includes a plurality of rotatable elements and the rotatable elements include constantly rotating elements rotating at uniform velocity and scanning elements, the method comprising:
   generating a function of corrected Fourier coefficients $(X=(X_j)_{(2N_{ho}+1) \times 1}=(I_0, A_1, B_1, A_2, B_2, \ldots, A_{N_{ho}}, B_{N_{ho}})^T)$ consisting of constant values $\kappa$, $d_{12}$, $d_{13}$, $l_1$, and $l_2$ of common factors, optical properties (a refractive index, a thickness of a thin film, a shape and a dimension of a nano pattern) of a sample, azimuths $\theta$ of the scanning elements, phase differences $\delta$ of compensators, an incident angle $\phi$, and a measurement wavelength $\lambda$;
   generating a Mueller matrix component vector $V^{(SP)}(X)$ of the sample consisting of the function of the corrected Fourier coefficients X;
   generating an ellipsometric parameter Q(X) of the sample consisting of the function of the corrected Fourier coefficients X from Mueller matrix components obtained in the generating of the Mueller matrix component vector;
   generating a theoretical equation on a sensitivity coefficient using the function of the corrected Fourier coefficients X using a partial derivative of $c_{Q,X_j}=\partial Q/\partial X_j$ from the ellipsometric parameter Q(X) of the sample generated in the generating of the ellipsometric parameter;
   generating a theoretical equation on a covariance of the corrected Fourier coefficients X; and
   generating a theoretical equation $\sigma(\langle Q \rangle)$ on standard deviations of ellipsometric parameters Q consisting of a function of a measurement frequency N required for computation of the Fourier coefficient, a measurement frequency J of exposure per one rotating period, a mechanical rotating period T of the constantly rotating element, a delay time $T_d$, an integration time $T_i$, a scaling coefficient $\kappa$, and the corrected Fourier coefficients X by substituting results of the generating of the theoretical equation on the sensitivity coefficient and the generating of the theoretical equation on the covariance into the following Equation $$\sigma(\langle Q \rangle) = \left[ \sum_{j=1}^{2N_{ho}+1} c_{Q,X_j}^2 \text{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \text{cov}(\langle X_j \rangle, \langle X_j \rangle) \right]^{1/2}$$

wherein, the theoretical equation on the corrected Fourier coefficients X is obtained from the generating of the function of the corrected Fourier coefficient, angle brackets ($<$ $>$) represent an average value for measurement values obtained by performing a total of N times measurements when the constantly rotating element performs measurement once for each mechanical rotation, $N_{ho}$ represents an uppermost index value among nonzero alternating current components of the Fourier coefficient, $\text{cov}(X_j, X_k)$ represents a covariance for the corrected Fourier coefficients $(X_j, X_k)$.

6. The method of claim 5, wherein the function of the corrected Fourier coefficients X in the generating of the function of the corrected Fourier coefficient depends on the following Equation $$I_0 = \gamma \sum_{j=1}^{u} \sum_{k=1}^{v} i_{0,jk} M_{jk} = \gamma i_0 \cdot V^{(SP)}$$

$$A_n = \gamma \sum_{j=1}^{u} \sum_{k=1}^{v} a_{n,jk} M_{jk} = \gamma a_n \cdot V^{(SP)}$$

$$B_n = \gamma \sum_{j=1}^{u} \sum_{k=1}^{v} b_{n,jk} M_{jk} = \gamma b_n \cdot V^{(SP)}$$

wherein, in the case of RE-SE in which a common factor $\gamma$ includes a scanning polarizer (azimuth P of the scanning polarizer) and a scanning analyzer (azimuth A of the scanning analyzer, $I_0$ represents a direct current (DC) component of the corrected Fourier coefficient, $A_n$ and $B_n$ represent the alternating current (AC) components of the corrected Fourier coefficient, $i_{0,jk}$ ($=\partial I_0/\partial M_{jk}$) represents a coefficient component in a linear equation for the DC component $I_0$ of the corrected Fourier coefficient, $a_{n,jk}$ ($=\partial A_n/\partial M_{jk}$) represents a coefficient component in a linear equation for the AC component $A_n$ of the corrected Fourier coefficient, $b_{n,jk}(\partial B_n/\partial M_{jk})$ represents a coefficient component in a linear equation for the AC component $B_n$ of the corrected Fourier coefficient, $M_{jk}$ represents one component of Mueller matrix $M^{(SP)}= (M_{jk})_{4\times 4}$ of a sample, $V^{(SP)}=(M_{11}, \ldots, M_{1v}, \ldots, M_{u1}, \ldots, M_{uv})^T$ is a vector consisting of Mueller matrix components of the sample, u and v are integers differently given depending on a kind of used RE-SE, superscript T is a sign representing a transposed matrix performing a transposition in a matrix, $\gamma = \kappa (1 + d_{12} \cos 2A + d_{13} \sin 2A)(1 + l_1 \cos 2P + l_2 \sin 2P)$, $\kappa = c\varepsilon_0 \eta_{QE} A_{PDE} T_{PSA} T_{PSG} D_{11} L_0 / 2$, c represents a speed of light under vacuum, $\varepsilon_0$ represents permittivity of vacuum, $\eta_{QE}$ represents quantum efficiency of a photodetector element, $A_{PDE}$ represents a measured effective area of the photodetector element, $T_{PSG}$ represents a transmission coefficient of a polarization state generator (PSG), $T_{PSA}$ represents a transmission coefficient of a polarization state analyzer (PSA), $L_0$, $L_1$, and $L_2$ represent Stokes vector components of a light wave just before being incident on PSG, $D_{11}$, $D_{12}$, and $D_{13}$ represents Mueller matrix components of detector optic system (DOS) disposed between a PSA and the photodetector element, $d_{12(13)} = D_{12(13)}/D_{11}$, $l_{1(2)} = L_{1(2)}/L_0$, $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$ is a vector consisting of coefficient components for 4, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$ is a vector consisting of coefficient components for $A_n$, $b_n = (\partial B_n/\partial M_{11}, \ldots, \partial B_n/\partial M_{1v}, \ldots, \partial B_n/\partial M_{u1}, \ldots, \partial B_n/\partial M_{uv})/\gamma$ is a vector consisting of coefficient components for $B_n$.

7. The method of claim 5, wherein the Mueller matrix component vector $V^{(SP)}(X)$ of the sample in the generating of the Mueller matrix component vector depends on the following Equation which is the function of the corrected Fourier coefficients X $$V^{(SP)} = (\Omega^T \Omega)^{-1} \Omega^T X$$

here, $\Omega = \gamma(i_0, a_1, b_1, a_2, b_2, \ldots, a_{N_{ho}}, b_{N_{ho}})^T$ and $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$ is a vector consisting of coefficient components for $I_0$, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$ is a vector consisting of coefficient components for $A_n$, $b_n = (\partial B_n/\partial M_{11}, \ldots, \partial B_n/\partial M_{1v}, \ldots, \partial B_n/\partial M_{u1}, \ldots, \partial B_n/\partial M_{uv})/\gamma$ is a vector consisting of coefficient components for $\beta_n$, $M_{jk}$ represents one component of Mueller matrix $M^{(SP)}= (M_{jk})_{4\times 4}$ of a sample, $V^{(SP)}=(M_{11}, \ldots, M_{1v}, \ldots, M_{u1}, \ldots, M_{uv})^T$ is a vector consisting of Mueller matrix components of the sample, u and v are integers differently given depending on a kind of used RE-SE, superscript T is a sign representing a transposed matrix performing a transposition in a matrix, superscript −1 is a sign representing an inverse matrix in the matrix, $X = (X_j)_{(2N_{ho}+1)\times 1} = (I_0, A_1, B_1, A_2, B_2, \ldots, A_{N_{ho}}, B_{N_{ho}})^T$ represents a vector of the corrected Fourier coefficients, $I_0$ represents a direct current (DC) component of the Fourier coefficient, $A_n$ and $B_n$ represent the alternating current (AC) components of the Fourier coefficient, and $N_{ho}$ represents an uppermost index value among nonzero alternating current components of the Fourier coefficient).

8. The method of claim 5, wherein the theoretical equation on the covariance between the corrected Fourier coefficients X in the generating of the theoretical equation on the covariance is obtained depending on $\text{cov}(\langle X_j \rangle, \langle X_k \rangle) \cong \text{cov}(\langle X_j' \rangle, \langle X_k' \rangle)$ from a theoretical equation on the covariance between uncorrected Fourier coefficients X', and the theoretical equation on the covariance between the uncorrected Fourier coefficients X' depends on the following Equation $$\text{cov}(\langle I_0' \rangle, \langle I_0' \rangle) = \sigma^2(\langle I_0' \rangle) = \frac{\eta}{NJT_i}\langle I_0' \rangle$$

$$\text{cov}(\langle A_n' \rangle, \langle A_n' \rangle) = \sigma^2(\langle A_n' \rangle) = \frac{2\eta\xi_n^2}{NJT_i\sin^2\xi_n}\left(\langle I_0' \rangle + \frac{\sin\xi_{2n}}{2\xi_{2n}}\langle A_{2n}' \rangle\right)$$

$$\text{cov}(\langle B_n' \rangle, \langle B_n' \rangle) = \sigma^2(\langle B_n' \rangle) = \frac{2\eta\xi_n^2}{NJT_i\sin^2\xi_n}\left(\langle I_0' \rangle - \frac{\sin\xi_{2n}}{2\xi_{2n}}\langle A_{2n}' \rangle\right)$$

$$\text{cov}(\langle I_0' \rangle, \langle A_n' \rangle) = \frac{\eta}{NJT_i}\langle A_n' \rangle$$

$$\text{cov}(\langle I_0' \rangle, \langle B_n' \rangle) = \frac{\eta}{NJT_i}\langle B_n' \rangle$$

$$\text{cov}(\langle A_n' \rangle, \langle A_m' \rangle) =$$
$$\frac{\eta m \xi_n}{NJT_i\sin\xi_n\sin\xi_m}\left(\frac{\sin\xi_{n+m}}{n+m}\langle A_{n+m}' \rangle + \frac{\sin\xi_{n-m}}{n-m}\langle A_{n-m}' \rangle\right), \quad (n \neq m),$$

$$\text{cov}(\langle B_n' \rangle, \langle B_m' \rangle) =$$
$$\frac{\eta m \xi_n}{NJT_i\sin\xi_n\sin\xi_m}\left(\frac{\sin\xi_{n-m}}{n-m}\langle A_{n-m}' \rangle - \frac{\sin\xi_{n+m}}{n+m}\langle A_{n+m}' \rangle\right), \quad (n \neq m),$$

$$\text{cov}(\langle A_n' \rangle, \langle B_m' \rangle) =$$
$$\begin{cases} \frac{\eta\xi_n}{NJT_i\tan\xi_n}\langle B_{2n}' \rangle, & (n = m), \\ \frac{\eta m \xi_n}{NJT_i\sin\xi_n\sin\xi_m}\left(\frac{\sin\xi_{n+m}}{n+m}\langle B_{n+m}' \rangle - \frac{\sin\xi_{n-m}}{n-m}\langle B_{n-m}' \rangle\right), & (n \neq m), \end{cases}$$

wherein, $\xi_n = n\pi T_i/T$, and angle brackets ($\langle \rangle$) represent an average value for measurement values obtained by performing a total of N times measurements when the constantly rotating element performs measurement once for each mechanical rotation.

9. The method of claim 5, further comprising:

calculating an optimum measurement condition for finding out a position of the azimuth θ of the scanning elements or the incidence angle φ having a minimum value of Z in a measurement precision assessment function Z depending on the following Equation, when the number of measurement wavelengths $\lambda_j$ is $N_\lambda$ and the number of kinds of ellipsometric parameters $Q_k(\lambda_j)$ of the sample is $N_Q$, wherein $$Z = \sqrt{\frac{1}{N_\lambda N_Q} \sum_{j=1}^{N_\lambda} \sum_{k=1}^{N_Q} \sigma^2(\langle Q_k(\lambda_j) \rangle)}.$$

* * * * *

UNITED STATES PATENT AND TRADEMARK OFFICE
CERTIFICATE OF CORRECTION

PATENT NO. : 9,581,498 B2
APPLICATION NO. : 14/969096
DATED : February 28, 2017
INVENTOR(S) : Yong Jai Cho et al.

Page 1 of 1

It is certified that error appears in the above-identified patent and that said Letters Patent is hereby corrected as shown below:

In the Claims

Column 23, Line 36, Claim 1, after "wherein," delete "represent"

Column 24, Line 67, Claim 5, delete "$\kappa$," and insert -- $\eta$, --

Column 25, Lines 6-11, Claim 5, delete

"$$\sigma(\langle Q \rangle) = \left[ \sum_{j=1}^{2N_{ho}+1} c_{Q,X_j}^2 \text{cov}(\langle X_j \rangle, \langle X_j \rangle) + 2 \sum_{j=1}^{2N_{ho}} \sum_{k=j+1}^{2N_{ho}+1} c_{Q,X_j} c_{Q,X_k} \text{cov}(\langle X_j \rangle, \langle X_j \rangle) \right]^{1/2}$$"

and insert $$\sigma(\langle Q \rangle) = \left[ \sum_{j=1}^{2N_{ho}+1} c_{Q,X_j}^2 \text{cov}\left(\langle X_j \rangle, \langle X_j \rangle\right) + 2 \sum_{j=1}^{2N_{ho}} \sum_{k=j+1}^{2N_{ho}+1} c_{Q,X_j} c_{Q,X_k} \text{cov}\left(\langle X_j \rangle, \langle X_k \rangle\right) \right]^{1/2}$$

--

Column 25, Line 58, Claim 6, delete "$b_{n,jk}(\partial B_n / \partial M_{jk})$" and insert -- $b_{n,jk}(=\partial B_n / \partial M_{jk})$ --

Column 25, Line 63, Claim 6, delete "$V^{(SP)}(M_{11}$," and insert -- $V^{(SP)}=(M_{11}$, --

Column 26, Line 29, Claim 6, delete "4," and insert -- $I_0$, --

Column 26, Line 52, Claim 7, delete "$\beta_n$," and insert -- $B_n$, --

Column 27, Lines 4-5, Claim 7, delete "coefficient)." and insert -- coefficient. --

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*